United States Patent
Cabiri et al.

(10) Patent No.: US 7,635,346 B2
(45) Date of Patent: Dec. 22, 2009

(54) PRESSURE-PROPELLED SYSTEM FOR BODY LUMEN

(75) Inventors: Oz Cabiri, Macabim (IL); Yossi Gross, Moshay Mazor (IL); Boris Degtiar, Modi'in (IL); Eran Shor, Bizaron (IL)

(73) Assignee: G. I. View Ltd., Ramat Gan (IL)

( * ) Notice: Subject to any disclaimer, the term of this patent is extended or adjusted under 35 U.S.C. 154(b) by 1064 days.

(21) Appl. No.: 10/967,922

(22) Filed: Oct. 18, 2004

(65) Prior Publication Data

US 2005/0197531 A1    Sep. 8, 2005

Related U.S. Application Data

(63) Continuation-in-part of application No. 10/838,648, filed on May 3, 2004, which is a continuation-in-part of application No. 10/753,424, filed on Jan. 9, 2004, and a continuation-in-part of application No. 10/753,424, filed on Jan. 9, 2004.

(60) Provisional application No. 60/607,986, filed on Sep. 8, 2004, provisional application No. 60/571,438, filed on May 14, 2004.

(51) Int. Cl.
*A61M 29/00* (2006.01)

(52) U.S. Cl. .................................................. 604/99.01

(58) Field of Classification Search ......... 604/523–539, 604/264, 96.01, 101.01–101.05, 102.01–102.03, 604/916, 917, 920, 921; 606/191–194
See application file for complete search history.

(56) References Cited

U.S. PATENT DOCUMENTS 3,924,625 A    12/1975    Peterson (Continued)

FOREIGN PATENT DOCUMENTS

EP    0242428    10/1987

(Continued)

OTHER PUBLICATIONS

U.S. Appl. No. 60/490,038.
English abstract of JP 2006026344 dated Feb. 2, 2006.

*Primary Examiner*—Manuel A Mendez
(74) *Attorney, Agent, or Firm*—Ladas & Parry LLP

(57) ABSTRACT

Apparatus is provided for use with a biologically-compatible-fluid pressure source, the apparatus including an elongate carrier, adapted to be inserted through a proximal opening of a body lumen, and a piston head coupled to a distal portion of the carrier. The piston head is adapted to form a pressure seal with a wall of the lumen after the carrier has been inserted into the lumen, and to be advanced distally through the body lumen in response to pressure from the fluid pressure source. The apparatus is configured to facilitate distal advancement of the piston head by facilitating passage of fluid out of the lumen from a site within the lumen distal to the piston head. The apparatus additionally includes an optical system, coupled to the carrier in a vicinity of the distal portion, the optical system having distal and proximal ends. The optical system includes an image sensor, positioned at the proximal end of the optical system; an optical member having distal and proximal ends, and shaped so as to define a lateral surface, at least a distal portion of which is curved, configured to provide omnidirectional lateral viewing; and a convex mirror, coupled to the distal end of the optical member, wherein the optical member and the mirror have respective rotational shapes about a common rotation axis.

15 Claims, 9 Drawing Sheets

U.S. PATENT DOCUMENTS

| | | |
|---|---|---|
| 4,040,413 A | 8/1977 | Ohshiro |
| 4,066,070 A | 1/1978 | Utsugi |
| 4,077,610 A | 3/1978 | Masuda |
| 4,148,307 A | 4/1979 | Utsugi |
| 4,176,662 A | 12/1979 | Frazer |
| 4,403,985 A | 9/1983 | Boretos |
| 4,530,698 A | 7/1985 | Goldstein et al. |
| 4,561,427 A | 12/1985 | Takada |
| 4,596,381 A | 6/1986 | Hamrick |
| 4,690,131 A | 9/1987 | Lyddy et al. |
| 4,838,859 A | 6/1989 | Strassmann |
| 4,971,034 A | 11/1990 | Doi et al. |
| 4,976,524 A | 12/1990 | Chiba |
| 5,259,364 A | 11/1993 | Bob et al. |
| 5,337,732 A | 8/1994 | Grundfest et al. |
| 5,353,807 A | 10/1994 | DeMarco |
| 5,364,353 A | 11/1994 | Corfitsen et al. |
| 5,395,332 A | 3/1995 | Ressemann et al. |
| 5,398,670 A | 3/1995 | Ortiz et al. |
| 5,471,988 A | 12/1995 | Fujio et al. |
| 5,509,371 A | 4/1996 | Phillips |
| 5,571,114 A | 11/1996 | Devanaboyina |
| 5,586,968 A | 12/1996 | Grundl et al. |
| 5,604,531 A | 2/1997 | Iddan et al. |
| 5,662,587 A | 9/1997 | Grundfest et al. |
| 5,728,068 A | 3/1998 | Leone et al. |
| 5,740,808 A | 4/1998 | Panescu et al. |
| 5,863,284 A | 1/1999 | Klein |
| 5,879,325 A | 3/1999 | Lindstrom et al. |
| 5,906,357 A | 5/1999 | Munson, Sr. |
| 5,906,591 A | 5/1999 | Dario et al. |
| 5,910,105 A | 6/1999 | Swain et al. |
| 5,941,815 A | 8/1999 | Chang |
| 5,984,860 A | 11/1999 | Shan |
| 6,007,482 A | 12/1999 | Madni et al. |
| 6,028,719 A | 2/2000 | Beckstead et al. |
| 6,071,234 A | 6/2000 | Takada |
| 6,157,018 A | 12/2000 | Ishiguro et al. |
| 6,277,065 B1 | 8/2001 | Donofrio |
| 6,296,608 B1 | 10/2001 | Daniels et al. |
| 6,315,713 B1 | 11/2001 | Takada |
| 6,332,865 B1 | 12/2001 | Begg et al. |
| 6,333,826 B1 | 12/2001 | Charles |
| 6,341,044 B1 | 1/2002 | Driscoll, Jr. et al. |
| 6,356,296 B1 | 3/2002 | Driscoll, Jr. et al. |
| 6,373,642 B1 | 4/2002 | Wallerstein et al. |
| 6,388,820 B1 | 5/2002 | Wallerstein et al. |
| 6,422,989 B1 | 7/2002 | Hektner |
| 6,424,377 B1 | 7/2002 | Driscoll, Jr. et al. |
| 6,449,103 B1 | 9/2002 | Charles |
| 6,459,451 B2 | 10/2002 | Driscoll, Jr. et al. |
| 6,485,409 B1 | 11/2002 | Voloshin et al. |
| 6,493,032 B1 | 12/2002 | Wallerstein et al. |
| 6,503,192 B1 | 1/2003 | Ouchi |
| 6,517,477 B1 | 2/2003 | Wendlandt |
| 6,527,705 B1 | 3/2003 | Ouchi |
| 6,537,206 B2 | 3/2003 | Takada |
| 6,544,216 B1 | 4/2003 | Sammler et al. |
| 6,597,520 B2 | 7/2003 | Wallerstein et al. |
| 6,599,237 B1 | 7/2003 | Singh |
| 6,611,282 B1 | 8/2003 | Trubko et al. |
| 6,648,814 B2 | 11/2003 | Kim et al. |
| 6,682,479 B1 | 1/2004 | Takahashi et al. |
| 6,695,771 B2 | 2/2004 | Takada |
| 6,702,734 B2 | 3/2004 | Kim et al. |
| 6,702,735 B2 | 3/2004 | Kelly |
| 6,704,148 B2 | 3/2004 | Kumata |
| 6,709,388 B1 | 3/2004 | Mosse et al. |
| 6,743,208 B1 | 6/2004 | Coyle |
| 6,764,441 B2 | 7/2004 | Chiel et al. |
| 6,786,864 B2 | 9/2004 | Matsuura et al. |
| 6,800,056 B2 | 10/2004 | Tartaglia et al. |
| 6,814,728 B2 | 11/2004 | Ouchi |
| 6,824,510 B2 | 11/2004 | Kim et al. |
| 6,827,718 B2 | 12/2004 | Hutchins et al. |
| 6,837,846 B2 | 1/2005 | Jaffe et al. |
| 6,866,626 B2 | 3/2005 | Long et al. |
| 6,869,393 B2 | 3/2005 | Butler |
| 6,911,005 B2 | 6/2005 | Ouchi et al. |
| 6,932,323 B2 | 8/2005 | James |
| 6,974,441 B2 | 12/2005 | Ravo |
| 7,056,283 B2 | 6/2006 | Baror et al. |
| 2002/0012059 A1 | 1/2002 | Wallerstein et al. |
| 2002/0072651 A1 | 6/2002 | Vilos |
| 2002/0107478 A1 | 8/2002 | Wendlandt |
| 2002/0109772 A1 | 8/2002 | Kuriyama et al. |
| 2002/0109773 A1 | 8/2002 | Kuriyama et al. |
| 2003/0000526 A1 | 1/2003 | Gobel |
| 2003/0074015 A1 | 4/2003 | Nakao |
| 2003/0083547 A1 | 5/2003 | Hamilton et al. |
| 2003/0105386 A1 | 6/2003 | Voloshin et al. |
| 2003/0168068 A1 | 9/2003 | Poole et al. |
| 2003/0181788 A1 | 9/2003 | Yokoi et al. |
| 2003/0191369 A1 | 10/2003 | Arai et al. |
| 2003/0208219 A1 | 11/2003 | Aznoian et al. |
| 2003/0225433 A1 | 12/2003 | Nakao |
| 2004/0004836 A1 | 1/2004 | Dubuc |
| 2004/0111010 A1 | 6/2004 | Nishiie |
| 2004/0143161 A1 | 7/2004 | Baror et al. |
| 2004/0199087 A1 | 10/2004 | Swain et al. |
| 2004/0199088 A1 | 10/2004 | Bakos et al. |
| 2004/0199196 A1 | 10/2004 | Ravo |
| 2004/0204702 A1 | 10/2004 | Ziegler et al. |
| 2004/0249247 A1 | 12/2004 | Iddan |
| 2004/0260150 A1 | 12/2004 | Bernstein |
| 2005/0038317 A1 | 2/2005 | Ratnakar |
| 2005/0038319 A1 | 2/2005 | Goldwasser et al. |
| 2005/0085841 A1 | 4/2005 | Eversull et al. |
| 2005/0095200 A1 | 5/2005 | Schwarzberg |
| 2005/0107664 A1 | 5/2005 | Kalloo et al. |
| 2005/0154355 A1 | 7/2005 | Gross et al. |
| 2005/0165272 A1 | 7/2005 | Okada et al. |

FOREIGN PATENT DOCUMENTS

| | | |
|---|---|---|
| EP | 0267446 | 5/1988 |
| EP | 0659387 | 6/1995 |
| FR | 1465723 | 3/1967 |
| JP | 7-313443 | 12/1995 |
| JP | 2006026344 | 2/2006 |
| WO | WO 00/44275 | 8/2000 |
| WO | WO 01/68540 | 9/2001 |
| WO | WO 02/059676 | 8/2002 |
| WO | WO 02/075348 | 9/2002 |
| WO | WO 03/026272 | 3/2003 |
| WO | WO 03/045487 | 6/2003 |
| WO | WO 03/046830 | 6/2003 |
| WO | WO 03/053225 | 7/2003 |
| WO | 2004/016299 | 2/2004 |
| WO | WO 2004/010858 | 2/2004 |
| WO | WO 2004/069057 | 8/2004 |
| WO | WO 2006/025045 | 3/2006 |

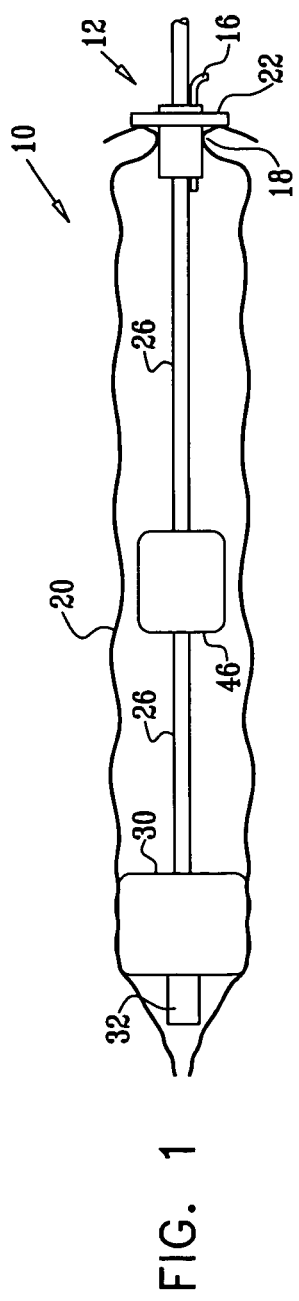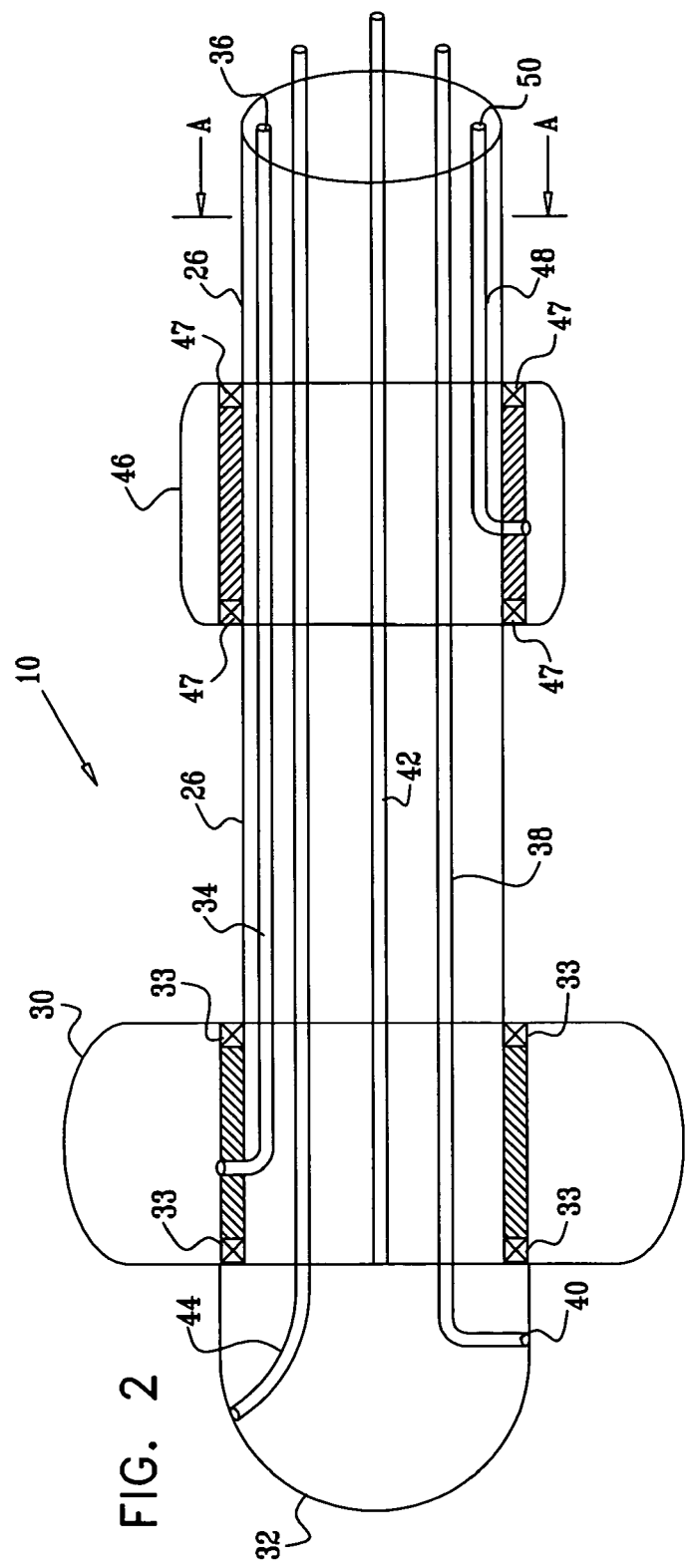
FIG. 1
FIG. 2

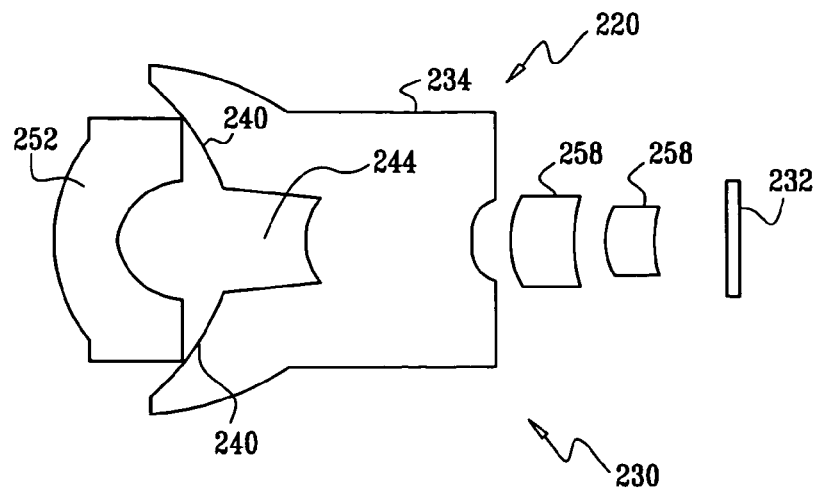
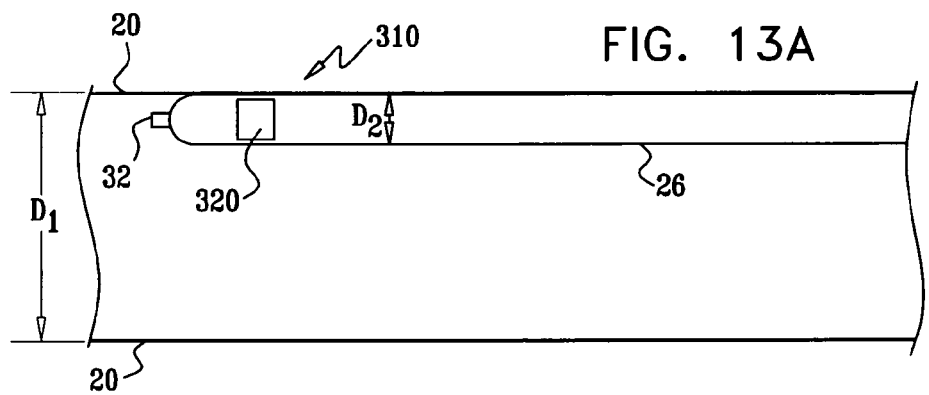
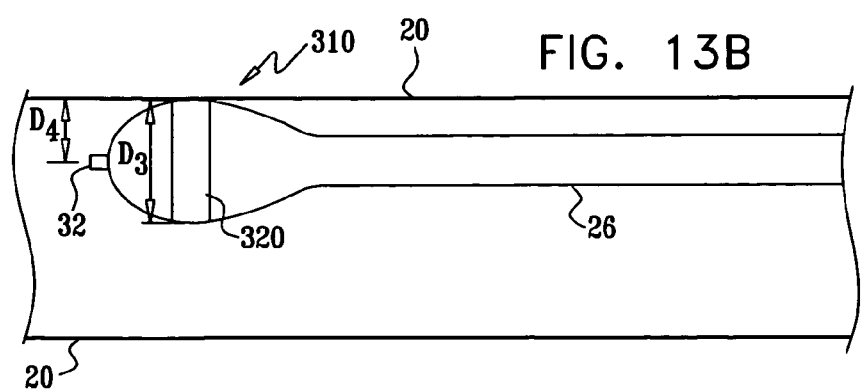

PRESSURE-PROPELLED SYSTEM FOR BODY LUMEN

CROSS-REFERENCES TO RELATED APPLICATIONS

The present application is a continuation-in-part of:

(a) U.S. patent application Ser. No. 10/838,648 to Gross et al., filed May 3, 2004, entitled, "Pressure-propelled system for body lumen," which is a continuation-in-part of U.S. patent application Ser. No. 10/753,424 to Gross et al., filed Jan. 9, 2004 entitled "Pressure-propelled system for body lumen" and a continuation-in-part of (b) U.S. patent application Ser. No. 10/753,424 to Gross et al., filed Jan. 9, 2004, entitled, "Pressure-propelled system for body lumen."

The present application claims priority (benefit) from:

(a) a U.S. provisional patent application 60/607,986 to Cabiri et al., filed Sep. 8, 2004, entitled, "Mechanical aspects of pressure-propelled system for body lumen," and (b) U.S. Provisional Patent Application 60/571,438 to Dotan et al., filed May 14, 2004, entitled, "Omnidirectional and forward-looking imaging device."

All of the above-mentioned applications are assigned to the assignee of the present application and are incorporated herein by reference.

FIELD OF THE INVENTION

The present invention relates generally to a pressure-propelled system, suitable for imaging body lumens, such as the gastrointestinal (GI) tract.

BACKGROUND OF THE INVENTION

Many imaging devices are known for producing medical images of body lumens, such as the gastrointestinal (GI) tract. For example, endoscopy is widely used for observing, photographing tissue, and taking specimens from lesions and the like. In a conventional method of examining a colon using an endoscope, for example, the endoscope is typically manually inserted into the colon. In this manual technique, patients may often complain of abdominal pain and distention because the colon is extended or excessively dilated, thereby necessitating stopping the endoscopic procedure. Furthermore, it is not unusual for the colon to bleed and be accidentally perforated. Insertion of an endoscope through the sigmoid colon and into the descending colon, or through the splenic flexure, the transverse colon, the hepatic flexure or parts affected by previous operations may also be accompanied with difficulty. Because of these reasons, a colonoscopy is typically performed by a relatively small number of skilled practitioners, and the rate of patient pain and discomfort is high.

U.S. Pat. No. 5,337,732 to Grundfest et al., whose disclosure is incorporated herein by reference, describes a robot for performing endoscopic procedures, which includes a plurality of segments attached to each other through an articulated joint. Actuators can move the segments together and apart and change their angular orientation to allow the robot to move in an inchworm or snake-like fashion through a cavity or lumen within a patient. Inflatable balloons around the segments inflate to brace a temporarily stationary segment against the lumen walls while other segments move. A compressed gas line attached to the back segment provides compressed gas to inflate the balloons and optionally to drive the actuators. The lead segment includes a television camera and biopsy arm or other sensors and surgical instruments.

U.S. Patent Application Publication 2003/0168068 to Poole and Young, whose disclosure is incorporated herein by reference, describes a method for lining a body cavity with a liner that contains two chambers by (a) selectively controlling fluid pressure in a first of the chambers so as cause the first chamber to evert and advance into said body cavity, and (b) selectively controlling fluid pressure in a second of said chambers to control the stiffness of the liner.

U.S. Patent Application Publication 2003/0105386 and U.S. Pat. No. 6,485,409 to Voloshin et al., whose disclosures are incorporated herein by reference, describe endoscopic apparatus comprising an inflatable sleeve, wherein inflating the sleeve causes an endoscope to be advanced into the colon.

U.S. Patent Application Publication 2002/0107478 to Wendlandt, whose disclosure is incorporated herein by reference, describes a self-propelled catheter, wherein pressurizing an everting tube coupled to the catheter advances the catheter into the body.

U.S. Pat. No. 6,702,735 to Kelly, whose disclosure is incorporated herein by reference, describes a device for moving a tool along a passage. The tool is coupled to an inflatable sheath, such that as the sheath is inflated it extends into the passage and carries the tool along.

U.S. Pat. No. 5,259,364 to Bob, et al., whose disclosure is incorporated herein by reference, describes an endoscopic device comprising a flexible eversion tube, wherein inflating the eversion tube causes an endoscope to be advanced into a body cavity.

U.S. Pat. No. 4,403,985 to Boretos, whose disclosure is incorporated herein by reference, describes a catheter containing ports near its distal end through which high pressure fluid is forced to advance and steer the catheter.

U.S. Pat. No. 4,176,662 to Frazer, whose disclosure is incorporated herein by reference, describes an endoscope having a propulsion mechanism and at least one transmitter at the distal end transmitting bursts of energy waves for tracking the position of the distal end. The propulsion mechanism consists of two radially expandable bladders separated by an axially expandable bellows with only the forward bladder attached to the distal end so that by expanding and contracting them in proper sequence, propulsion of the endoscope is achieved.

U.S. Pat. No. 4,148,307 to Utsugi, whose disclosure is incorporated herein by reference, describes a tubular medical instrument having at least one cuff assembly including two cuffs disposed on the circumference of a flexible sheath, spaced at prescribed intervals and made expansible only in a radial direction of the flexible sheath, and a deformable propellant cuff having a doubled-back section, disposed also on the circumference of the sheath between the two cuffs. When air is introduced into, or drawn from, the three cuffs selectively, the flexible sheath automatically advances step-by-step in a human body cavity.

U.S. Pat. No. 5,906,591 to Dario et al., whose disclosure is incorporated herein by reference, describes an endoscopic robot, adapted to be inserted into a body cavity of a patient and to be advanced therein using "inchworm-like" motion.

U.S. Pat. No. 6,007,482 to Madni et al., whose disclosure is incorporated herein by reference, describes an endoscope having a pair of telescoping sections at its distal end, one of which carries a camera, and which are alternately actuated to provide movement through a body passageway by a Bowden type of cable. Respectively attached to the two cylindrical sections are inflatable bladders which provide for the movement.

U.S. Pat. No. 5,662,587 to Grundfest et al., whose disclosure is incorporated herein by reference, describes an endoscopic robot having a plurality of segments attached to each other. Traction segments embrace the walls of a body lumen. Other segments include actuators that cause the endoscope to locally deform its shape via bending, extending, or some combination of bending and extension. A method is provided to sequence the action of the segments to cause "inchworm-like" or "snake-like" locomotion, or a combination of them through a curved and flexible lumen. A compressed gas line attached to the back segment provides compressed gas for insufflation of the lumen, and can optionally be used to drive the actuators that control the operation of the endoscope segments.

U.S. Pat. No. 4,690,131 to Lyddy, Jr. et al., whose disclosure is incorporated herein by reference, describes a combination of elements adapted to be used with an endoscope, and capable of at least partially extending with the instrument into the lumen of a tubular body part, such as the large intestine. A sheath is adapted to be mounted on the endoscope. The endoscope and sheath are provided with selectively inflatable cuffs movable with respect to one another by axially sliding the sheath on the endoscope.

U.S. Pat. No. 4,040,413 to Ohshiro, which is incorporated herein by reference, describes an endoscope comprising a tube having one or more inflatable balloons on an outer surface thereof. A fiber optic bundle passes through the tube to a distal flexible portion of the tube, for viewing an interior of a body cavity. When only one balloon is provided, the balloon is provided on one side of the tube near the end thereof to enlarge the space within a body cavity in one direction so that there is sufficient space in this direction for the flexible portion of the tube to bend in this direction, and to thereby obtain a large field of view. When more than one balloon is provided, one of the balloons is selectively inflated to enlarge the space within the body cavity in the desired direction. In an embodiment, an outer sleeve is provided around the tube with balloons on the outer face thereof and is made slidable with respect to the tube. The outer sleeve and the tube are inserted into the body cavity by alternately inflating the balloons on the outer sleeve and those on the tube to facilitate the insertion thereof into the body cavity.

U.S. Pat. No. 6,503,192 to Ouchi, which is incorporated herein by reference, describes an insertion facilitating device for an intestinal endoscope. The device has a cylindrical body in which an insertion portion of the endoscope is inserted while holding an anal sphincter of a patient in an open position. The cylindrical body is provided at one end thereof with a conical opening. In an embodiment, the cylindrical body is provided on its inner surface with a pressure leakage prevention ring made of a sponge material, for preventing leakage of internal air of the patient's body.

U.S. Patent Application Publication 2003/0083547 to Hamilton et al., which is incorporated herein by reference, describes methods and apparatus for inhibiting longitudinal expansion of a body portion of an endoscopic sheath during inflation of an inflatable member. In one embodiment, a sheath assembly includes a body portion adapted to encapsulate a distal end of an insertion tube, and an inflatable member coupled to the body portion and adapted to be inflated radially outwardly from the body portion. The sheath assembly further includes an expansion-inhibiting mechanism coupled to at least one of the inflatable member and the body portion. The expansion-inhibiting mechanism is described as inhibiting longitudinal expansion of the body portion during inflation of the inflatable member. The expansion-inhibiting mechanism may comprise, for example, a non-compliant member, a longitudinally-stretched portion, a reinforcing spring member, a pressure relief device, or a suitable detent mechanism.

PCT Publication WO 04/069057 to Gobel, which is incorporated herein by reference, describes a device for use in healing processes, comprising a flexible double-walled inflatable tube segment which encloses a hollow space.

U.S. Patent Application Publication 2003/0000526 to Gobel, which is incorporated herein by reference, describes techniques for controlling the breathing gas flow of a ventilator for assisted or controlled ventilation of a patient as a function of the tracheobronchial airway pressure of the patient. The techniques include introducing a ventilator tube, such as a tracheal tube or tracheostomy tube, into the trachea. The tube is subjected to breathing gas, and is equipped with an inflatable cuff and at least one lumen that is continuous from the distal end of the tube to the proximal end of the tube. The tube is adapted to detect the airway pressure by continuous or intermittent detection and evaluation of the intra-cuff pressure prevailing in the cuff of the tube. The breathing gas flow of the ventilator is controlled as a function of the intra-cuff pressure detected.

PCT Publication WO 03/045487 to Gobel, which is incorporated herein by reference, describes a bladder catheter for transurethral introduction into the urinary bladder by the urethrae, consisting of an elastic catheter shank with a fillable balloon element secured thereto and connected to a filling channel incorporated into the wall of the catheter shank. The balloon element and the catheter shank are made of polyurethane, a polyurethane-polyvinylchloride mixture, or similar polyurethane-based material.

SUMMARY OF THE INVENTION

Some embodiments of the present invention provide an imaging system which is propelled by fluid pressure through a body lumen, such as the gastrointestinal (GI) tract. Embodiments of the invention are described hereinbelow with reference to the GI tract, but it is understood that these embodiments are not limited to use in the GI tract, and may be used for other body lumens as well. Unlike the prior art, which may inflate and anchor balloons and similar devices to the GI tract wall in an attempt to overcome the low friction of the GI tract, these embodiments of the present invention utilize the very low friction environment of the GI tract to propel the imaging system, typically with no need for anchoring.

There is thus provided, in accordance with an embodiment of the present invention, a system including a guide member at least partially insertable into a proximal opening of a body lumen, the guide member including a first passageway connectable to a source of fluid pressure, an elongate carrier arranged for sliding movement through the guide member, and a piston head mounted on the carrier, wherein a greater fluid pressure acting on a proximal side of the piston head than on a distal side of the piston head propels the piston head and the carrier in a distal direction in the body lumen.

The system of this embodiment of the invention may have different features. For example, the piston head may be inflatable. The carrier may include a second passageway in fluid communication with the piston head, which may be connected to a source of fluid pressure for inflating the piston head. A vent tube may pass through the piston head, having an opening distal to the piston head through which fluid may be vented to the outside. An image-capturing device may be mounted on the carrier, such as distal to the piston head. A power supply tube may pass through the carrier and may be connected to the image-capturing device. A fluid supply tube may pass through the carrier and may be connected to a fluid source.

In accordance with an embodiment of the present invention, an auxiliary piston head may be mounted on the carrier proximal to the first-mentioned piston head. The auxiliary piston head, which may be inflatable, may be fixed axially to the carrier at a fixed or variable distance from the first-mentioned piston head. The carrier may include a third passageway in fluid communication with the auxiliary piston head, which may be connected to a source of fluid pressure for inflating the auxiliary piston head.

There is therefore provided, in accordance with an embodiment of the present invention, apparatus for use with a biologically-compatible-fluid pressure source, including:

an elongate carrier, adapted to be inserted through a proximal opening of a body lumen; and a distal piston head coupled to a distal portion of the carrier and adapted to:
 be in direct contact with a wall of the lumen when the carrier is inserted into the lumen,
 be advanced distally through the body lumen in response to pressure from the fluid pressure source, and
 facilitate passage of fluid out of the lumen from a site within the lumen distal to the piston head.

In an embodiment, an outer surface of the piston head in contact with the wall of the lumen includes a low friction coating suitable for facilitating sliding of the piston head against the wall of the lumen.

In an embodiment, the lumen includes a gastrointestinal (GI) tract, and the piston head is adapted to be in direct contact with a wall of the GI tract when the carrier is inserted into the GI tract. For example, the GI tract may include a colon, and the piston head may be adapted to be in direct contact with a wall of the colon when the carrier is inserted into the colon.

In an embodiment, the apparatus includes a vent tube, and the piston head is adapted to facilitate the passage of the fluid out of the lumen through the vent tube. For some applications, the vent tube is shaped to define an inner diameter thereof that is between 1 and 5 millimeters, e.g., between 1 and 3 millimeters. In an embodiment, the vent tube is adapted to passively permit the passage of the fluid out of the lumen. Alternatively, the vent tube is adapted to be coupled to a suction source, whereby to actively facilitate the passage of the fluid out of the lumen. For example, the vent tube may be adapted to be coupled to the suction source such that during operation of the apparatus, a pressure distal to the piston head is between −5 millibar and +15 millibar.

In an embodiment, the piston head is adapted to be inflated so as to attain and maintain the direct contact with the wall of the colon.

For some applications:
 (i) the apparatus includes an auxiliary piston head, coupled to the carrier at a position proximal to the distal piston head,
 (ii) the auxiliary piston head is adapted to be inflated so as to attain and maintain direct contact with the wall of the colon, and
 (iii):
  (a) at at least one time while the carrier is within the body lumen, the distal piston head is adapted to be in a state of being already deflated at least in part simultaneously with the auxiliary piston head being already inflated and being advanced distally through the colon in response to pressure from the fluid pressure source, and
  (b) at at least one other time while the carrier is within the body lumen, the auxiliary piston head is adapted to be in a state of being already deflated at least in part simultaneously with the distal piston head being already inflated and being advanced distally through the colon in response to pressure from the fluid pressure source.

In an embodiment, the piston head is adapted to be intermittently deflated at least in part, while in the colon, whereby to facilitate the passage of the fluid out of the lumen from the site within the lumen distal to the piston head.

In an embodiment, the apparatus includes a piston-head-pressure sensor, adapted to sense a pressure within the piston head. Alternatively or additionally, the apparatus includes a distal pressure sensor, adapted to sense a pressure within the colon distal to the piston head. Further alternatively or additionally, the apparatus includes a proximal pressure sensor, adapted to sense a pressure within the colon proximal to the piston head. For some applications, one, two, or three of these sensors are provided.

In an embodiment, the apparatus includes:
 a pressure sensor, adapted to measure a first pressure associated with operation of the apparatus; and
 a control unit, adapted to regulate a second pressure associated with operation of the apparatus responsive to the measurement of the pressure sensor.

For example, the pressure sensor may be adapted to measure a pressure selected from the list consisting of: a pressure distal to the piston head, a pressure proximal to the piston head, and a pressure within the piston head.

In an embodiment, the control unit is adapted to regulate the pressure being measured by the pressure sensor. Alternatively, the control unit is adapted to regulate a pressure other than that being measured by the pressure sensor.

In an embodiment, the piston head is shaped to define a proximal lobe and a distal lobe, the lobes being in fluid communication with each other.

For some applications:
 (a) a volume of a first one of the lobes is adapted to decrease in response to a constriction of the colon adjacent thereto,
 (b) a volume of a second one of the lobes is adapted to remain constant in the absence of a change in colon diameter adjacent thereto, even if the volume of the first lobe is decreased, and/or
 (c) a pressure within the first and second lobes is equal in steady state, regardless of the decrease in volume of the first lobe.

In an embodiment, the piston head is adapted to be at an inflation pressure between 10 and 60 millibar during advancement through the colon (e.g., 20-50 millibar, or 30-45 millibar). Alternatively or additionally, the piston head is adapted to advance through the colon in response to a pressure from the fluid pressure source that is between 30% and 100% of the inflation pressure. For example, the piston head may be adapted to advance through the colon in response to a pressure from the fluid pressure source that is between 50% and 100% of the inflation pressure (e.g., between 50% and 80% of the inflation pressure).

In an embodiment, the piston head is shaped to define a distally-narrowing portion, and is adapted to be inserted into the colon such that a tip of the distally-narrowing portion points in a distal direction when the piston head is in the colon. For some applications, a proximal base of the distally-narrowing portion has a characteristic fully-inflated diameter that is larger than a diameter of at least a part of the colon through which the distally-narrowing portion is adapted to pass, whereby the base of the distally-narrowing portion does not inflate fully when the base is in that part of the colon.

There is further provided, in accordance with an embodiment of the present invention, a method, including:

placing a distal piston head in direct contact with a wall of a body lumen;

applying fluid pressure to the distal piston head to advance the piston head distally through the body lumen; and facilitating passage of fluid out of the lumen from a site within the lumen distal to the piston head.

In an embodiment, the method includes applying a low friction coating to an outer surface of the piston head intended for contact with the wall of the lumen, the low friction coating being suitable for facilitating sliding of the piston head against the wall of the lumen.

In an embodiment, the lumen includes a gastrointestinal (GI) tract, and placing the piston head includes placing the piston head in direct contact with a wall of the GI tract. In an embodiment, the GI tract includes a colon, and placing the piston head includes placing the piston head in direct contact with a wall of the colon.

In an embodiment, facilitating the passage of the fluid includes facilitating the passage of the fluid out of the lumen through a vent tube extending from the site distal to the piston head to a site outside of the lumen. For some applications, facilitating the passage of the fluid includes passively permitting the passage of the fluid through the vent tube and out of the lumen. Alternatively, facilitating the passage of the fluid includes actively removing the fluid from the lumen. For example, actively removing the fluid may include applying to the site distal to the piston head a pressure between −5 millibar and +15 millibar.

In an embodiment, placing the piston head in direct contact with the wall includes inflating the piston head to an extent sufficient to attain and maintain the direct contact with the wall of the colon.

In an embodiment, the method includes:

placing an auxiliary piston head proximal to the distal piston head;

inflating the auxiliary piston head to an extent sufficient to attain and maintain direct contact with the wall of the colon;

at at least one time while the distal piston head is within the body lumen, deflating the distal piston head at least in part, such that at a post-distal-piston-head-deflation time when the distal piston head is in a state of being already deflated at least in part, the auxiliary piston head is inflated and advancing distally through the colon in response to the applied fluid pressure; and at at least one other time while the distal piston head is within the body lumen, deflating the auxiliary piston head at least in part, such that at a post-auxiliary-piston-head-deflation time when the auxiliary piston head is in a state of being already deflated at least in part, the distal piston head is inflated and advancing distally through the colon in response to the applied pressure.

In an embodiment, facilitating the passage of the fluid out of the lumen includes intermittently deflating the piston head at least in part.

In an embodiment, the method includes sensing a pressure within the piston head, within the colon distal to the piston head, and/or within the colon proximal to the piston head.

In an embodiment, the method includes:

sensing a first pressure associated with performing the method; and regulating a second pressure associated with performing the method, responsive to sensing the first pressure.

For example, sensing the first pressure may include sensing a pressure selected from the list consisting of: a pressure distal to the piston head, a pressure proximal to the piston head, and a pressure within the piston head.

For some applications, regulating the second pressure includes regulating the first pressure. Alternatively, regulating the second pressure does not include regulating the first pressure.

In an embodiment, inflating the piston head includes inflating the piston head at an inflation pressure between 10 and 60 millibar. Alternatively or additionally, applying the fluid pressure includes setting the fluid pressure to between 30% and 100% of the inflation pressure (e.g., between 50% and 100% of the inflation pressure, or between 50% and 80% of the inflation pressure).

In an embodiment, inflating the piston head includes inflating the piston head at an inflation pressure between 20 and 50 millibar (e.g., between 30 and 45 millibar).

There is therefore provided, in accordance with an embodiment of the present invention, apparatus for use with a biologically-compatible-fluid pressure source, including:

an elongate carrier, adapted to be inserted through a proximal opening of a body lumen;

a distal piston head coupled to a distal portion of the carrier and adapted to:
  be in direct contact with a wall of the lumen after the carrier has been inserted into the lumen,
  be advanced distally through the body lumen in response to pressure from the fluid pressure source, and
  facilitate passage of fluid out of the lumen from a site within the lumen distal to the piston head; and an optical system having distal and proximal ends, and including:
  an image sensor, positioned at the proximal end of the optical system;
  an optical member having distal and proximal ends, and shaped so as to define a lateral surface, at least a distal portion of which is curved, configured to provide omnidirectional lateral viewing; and
  a convex mirror, coupled to the distal end of the optical member, wherein the optical member and the mirror have respective rotational shapes about a common rotation axis.

For some applications, the convex mirror is shaped so as define an opening through which distal light can pass.

There is also provided, in accordance with an embodiment of the present invention, apparatus for use with a biologically-compatible-fluid pressure source, including:

an elongate carrier, adapted to be inserted through a proximal opening of a body lumen;

an inflatable distal piston head coupled to a distal portion of the carrier, the distal piston head shaped so as to define a proximal lobe and a distal lobe in fluid communication with each other, the distal piston head adapted to:
  be inflated so as to attain direct contact with a wall of the lumen after the carrier has been inserted into the lumen, and
  be advanced distally through the body lumen in response to pressure from the fluid pressure source; and a flexible vent tube, passing through the proximal and distal lobes of the piston head, and opening to a site within the lumen distal to the piston head, and adapted to facilitate passage of fluid from the site.

There is further provided, in accordance with an embodiment of the present invention, apparatus including:

an elongate carrier, adapted to be inserted through a proximal opening of a body lumen;

a balloon coupled to a distal portion of the carrier and adapted to be in direct contact with a wall of the lumen after the carrier has been inserted into the lumen; and a hydrophilic substance disposed at an external surface of the balloon.

There is still further provided, in accordance with an embodiment of the present invention, apparatus including:

an elongate carrier, adapted to be inserted through a proximal opening of a body lumen; and a balloon coupled to a distal portion of the carrier and adapted to be in direct contact with a wall of the lumen after the carrier has been inserted into the lumen, the balloon having a characteristic thickness of no more than 20 microns.

For some applications, the balloon has a characteristic thickness of no more than 10 microns.

There is additionally provided, in accordance with an embodiment of the present invention, apparatus for use with a biologically-compatible-fluid pressure source, including:

an elongate carrier, adapted to be inserted through a proximal opening of a body lumen; and a distal piston head coupled to a distal portion of the carrier and adapted to:

be in direct contact with a wall of the lumen after the carrier has been inserted into the lumen, and be withdrawn proximally through the body lumen in response to pressure from the fluid pressure source.

For some applications, the carrier is adapted to facilitate passage of fluid out of the lumen from a site within the lumen proximal to the piston head.

There is yet additionally provided, in accordance with an embodiment of the present invention, apparatus for use with an elongate carrier for insertion through a proximal opening of a body lumen, the apparatus including:

an annular balloon, shaped so as to form an opening therethrough for insertion of the carrier, the balloon expandable to form a seal between the balloon and a wall of the body lumen in a vicinity of the proximal opening;

first and second fluid pressure sources;

a first tube, coupled between the first pressure source and an interior of the balloon; and a second tube, coupled between the second pressure source and an interior of the lumen distal to the annular balloon.

For some applications, at least one of the first and second pressure sources is adapted to be positioned outside the body lumen.

There is also provided, in accordance with an embodiment of the present invention, apparatus including:

an elongate carrier, adapted to be inserted through a proximal opening of a body lumen; and an inflatable cuff, shaped so as to define an opening therethrough through which the carrier can be inserted, the cuff adapted to form a seal with a wall of the body lumen when the cuff is in an inflated state in a vicinity of the proximal opening.

There is further provided, in accordance with an embodiment of the present invention, apparatus for use with a fluid source, the apparatus including:

an elongate carrier, adapted to be inserted through a proximal opening of a body lumen;

an image-capturing device, fixed to the carrier in a vicinity of a distal end of the carrier; and at least one fluid supply tube coupled to the carrier, the tube coupled to the fluid source, wherein the distal end of the carrier is shaped so as to define one or more openings in fluid communication with the tube, the openings oriented so as to spray at least a portion of the image-capturing device when fluid is provided by the fluid source.

There is still further provided, in accordance with an embodiment of the present invention, apparatus for use in a body lumen having a proximal opening and a wall, the apparatus including:

an elongate carrier, adapted to be inserted through the proximal opening of the body lumen;

an image-capturing device, fixed in a first vicinity of a distal end of the carrier, and adapted to provide omnidirectional lateral viewing; and an inflation element, fixed in a second vicinity of the distal end, and adapted to increase a diameter of the carrier in the second vicinity to an extent sufficient to position the image-capturing device a distance from the wall sufficient to enable omnidirectional focusing of the image-capturing device.

There is additionally provided, in accordance with an embodiment of the present invention, apparatus for use in a body lumen having a proximal opening, the apparatus including:

first and second fluid pressure sources;

an elongate carrier, adapted to be inserted through the proximal opening of the body lumen;

a distal inflatable piston head coupled to a distal portion of the carrier, and adapted to be in direct contact with a wall of the lumen after the carrier has been inserted into the lumen;

a first passageway in fluid communication with the first pressure source and a proximal portion of the lumen proximal to the piston head;

a second passageway in fluid communication with the second pressure source and the piston head;

first and second pressure sensors, adapted to measure pressure in the proximal portion of the lumen, and in the piston head, respectively; and a control unit, adapted to cause the piston head to be advanced distally in the lumen by:

while the first pressure source applies a pressure to the proximal portion of the lumen, driving the second pressure source to regulate a pressure in the piston head to be equal to the pressure in the proximal portion of the lumen plus a positive value.

For some applications, the apparatus includes a third passageway in fluid communication with a portion of the lumen distal to the piston head and a site outside the lumen.

There is yet additionally provided, in accordance with an embodiment of the present invention, apparatus for use with a biologically-compatible-fluid pressure source, including:

an elongate carrier, adapted to be inserted through a proximal opening of a body lumen;

a piston head coupled to a distal portion of the carrier and adapted to:

form a pressure seal with a wall of the lumen after the carrier has been inserted into the lumen, and be advanced distally through the body lumen in response to pressure from the fluid pressure source, the apparatus being configured to facilitate distal advancement of the piston head by facilitating passage of fluid out of the lumen from a site within the lumen distal to the piston head; and an optical system, coupled to the carrier in a vicinity of the distal portion, the optical system having distal and proximal ends, and including:

an image sensor, positioned at the proximal end of the optical system;

an optical member having distal and proximal ends, and shaped so as to define a lateral surface, at least a distal portion of which is curved, configured to provide omnidirectional lateral viewing; and a convex mirror, coupled to the distal end of the optical member, wherein the optical member and the mirror have respective rotational shapes about a common rotation axis.

In an embodiment, the lumen includes a gastrointestinal (GI) tract, and the carrier is adapted to be inserted through the proximal opening of the GI tract. In an embodiment, the GI tract includes a colon, and the carrier is adapted to be inserted through the proximal opening of the colon.

In an embodiment, the piston head is adapted to be in direct contact with the wall of the GI tract after the carrier has been inserted into the GI tract.

For some applications, the convex mirror is shaped so as to define an opening through which distal light can pass. For some applications, the optical member is shaped so as to define a distal indentation in the distal end of the optical member. For some applications, the optical member is shaped so as to define a proximal indentation in the proximal end of the optical member. For some applications, the optical system includes a distal lens, positioned distal to the mirror, the distal lens having a rotational shape about the common rotation axis. For some applications, the optical system is configured to provide different levels of magnification for distal light arriving at the image sensor through the distal end of the optical system, and lateral light arriving at the image sensor through the curved distal portion of the lateral surface of the optical member.

For some applications, an outer surface of the piston head forming the pressure seal with the wall of the GI tract includes a low friction coating suitable for facilitating sliding of the piston head against the wall of the GI tract.

For some applications, the apparatus includes a fluid source, and at least one fluid supply tube coupled to the carrier, the tube in fluid communication with the fluid source, and the distal portion of the carrier is shaped so as to define one or more openings in fluid communication with the tube, the openings oriented so as to spray at least a portion of the optical member when fluid is provided by the fluid source.

For some applications, the apparatus includes an inflation element, fixed in a vicinity of the distal portion of the carrier, and adapted to increase a diameter of the carrier in the vicinity to an extent sufficient to position the optical member a distance from the wall sufficient to enable omnidirectional focusing of the optical system.

In an embodiment, the apparatus includes a vent tube, and the apparatus is adapted to facilitate the passage of the fluid out of the GI tract through the vent tube. For some applications, the vent tube is adapted to passively permit the passage of the fluid out of the GI tract. Alternatively, the vent tube is adapted to be coupled to a suction source, whereby to actively facilitate the passage of the fluid out of the GI tract.

In an embodiment, the piston head is adapted to be inflated so as to form and maintain the pressure seal with the wall of the GI tract. For some applications, the piston head is adapted to be intermittently deflated at least in part, while in the GI tract, whereby to facilitate the passage of the fluid out of the GI tract from the site within the GI tract distal to the piston head. For some applications, the piston head is shaped to define a proximal lobe and a distal lobe, the lobes being in fluid communication with each other.

For some applications, the apparatus includes a piston-head-pressure sensor, adapted to sense a pressure within the piston head. For some applications, the piston-head-pressure sensor is adapted to be disposed within the piston head. Alternatively, the piston-head-pressure sensor is adapted to be disposed in a vicinity of the proximal opening of the GI tract.

For some applications, the piston-head-pressure sensor is adapted to be disposed outside of the GI tract.

There is also provided, in accordance with an embodiment of the present invention, apparatus for use with a biologically-compatible-fluid pressure source, including:

an elongate carrier, adapted to be inserted through a proximal opening of a body lumen; and an inflatable piston head coupled to a distal portion of the carrier, the piston head shaped so as to define a proximal lobe and a distal lobe in fluid communication with each other, the piston head adapted to:

be inflated so as to form a pressure seal with a wall of the lumen after the carrier has been inserted into the lumen, and be advanced distally through the body lumen in response to pressure from the fluid pressure source.

In an embodiment, the lumen includes a gastrointestinal (GI) tract, and the carrier is adapted to be inserted through the proximal opening of the GI tract. In an embodiment, the GI tract includes a colon, and the carrier is adapted to be inserted through the proximal opening of the colon.

In an embodiment, the piston head is adapted to be in direct contact with the wall of the GI tract after the carrier has been inserted into the GI tract.

For some applications, a volume of a first one of the lobes is adapted to decrease in response to a constriction of the GI tract adjacent thereto, a volume of a second one of the lobes is adapted to remain constant in the absence of a change in GI tract diameter adjacent thereto, even if the volume of the first lobe is decreased, and a pressure within the first and second lobes is equal in steady state, regardless of the decrease in volume of the first lobe.

For some applications, the distal lobe has a diameter substantially equal to a diameter of the GI tract. For some applications, the distal lobe has a length of between 3 and 5 cm. For some applications, the piston head is shaped so as to define at least one lobe in addition to the first and second lobes.

For some applications, the piston head is shaped so as to define an intermediate portion at which the proximal and distal lobes articulate. For some applications, the intermediate portion has a diameter equal to between 10% and 40% of a diameter of the distal lobe.

In an embodiment, the apparatus includes a flexible vent tube, passing through the proximal and distal lobes of the piston head, and opening to a site within the GI tract distal to the piston head, and adapted to facilitate distal advancement of the piston head by facilitating passage of fluid from the site. For some applications, the apparatus includes a suction source, adapted to actively facilitate the passage of the fluid from the site.

For some applications, a volume of a first one of the lobes is adapted to decrease in response to a constriction of the GI tract adjacent thereto, a volume of a second one of the lobes is adapted to remain constant in the absence of a change in GI tract diameter adjacent thereto, even if the volume of the first lobe is decreased, and a pressure within the first and second lobes is equal in steady state, regardless of the decrease in volume of the first lobe.

For some applications, the distal lobe has a diameter substantially equal to a diameter of the GI tract. For some applications, the distal lobe has a length of between 3 and 5 cm. For some applications, the piston head is shaped so as to define at least one lobe in addition to the first and second lobes.

For some applications, the piston head is shaped so as to define an intermediate portion at which the proximal and distal lobes articulate. For some applications, the intermediate portion has a diameter equal to between 10% and 40% of a diameter of the distal lobe.

There is further provided, in accordance with an embodiment of the present invention, apparatus including:

an elongate carrier, adapted to be inserted through a proximal opening of a body lumen;

a balloon coupled to a distal portion of the carrier and adapted to be in direct contact with a wall of the lumen after the carrier has been inserted into the lumen; and a hydrophilic substance disposed at an external surface of the balloon.

In an embodiment, the lumen includes a gastrointestinal (GI) tract, and the carrier is adapted to be inserted through the proximal opening of the GI tract. In an embodiment, the GI tract includes a colon, and the carrier is adapted to be inserted through the proximal opening of the colon.

For some applications, the balloon is shaped so as to define a proximal lobe and a distal lobe, the lobes being in fluid communication with each other.

There is still further provided, in accordance with an embodiment of the present invention, apparatus including:

an elongate carrier, adapted to be inserted through a proximal opening of a body lumen; and a balloon coupled to a distal portion of the carrier and adapted to be in direct contact with a wall of the lumen after the carrier has been inserted into the lumen, an outer surface of the balloon in contact with the wall of the lumen including a low friction coating suitable for facilitating sliding of the balloon against the wall of the lumen.

In an embodiment, the lumen includes a gastrointestinal (GI) tract, and the carrier is adapted to be inserted through the proximal opening of the GI tract. In an embodiment, the GI tract includes a colon, and the carrier is adapted to be inserted through the proximal opening of the colon.

For some applications, the low friction coating includes a lubricant.

For some applications, the balloon is shaped so as to define a proximal lobe and a distal lobe, the lobes being in fluid communication with each other.

There is additionally provided, in accordance with an embodiment of the present invention, apparatus including:

an elongate carrier, adapted to be inserted through a proximal opening of a body lumen; and a balloon coupled to a distal portion of the carrier and adapted to be in direct contact with a wall of the lumen after the carrier has been inserted into the lumen, the balloon having a characteristic thickness of no more than 20 microns.

In an embodiment, the lumen includes a gastrointestinal (GI) tract, and the carrier is adapted to be inserted through the proximal opening of the GI tract. In an embodiment, the GI tract includes a colon, and the carrier is adapted to be inserted through the proximal opening of the colon.

For some applications, the balloon has a characteristic thickness of no more than 10 microns. For some applications, an outer surface of the balloon in contact with the wall of the GI tract includes a low friction coating suitable for facilitating sliding of the balloon against the wall of the GI tract. For some applications, an outer surface of the balloon in contact with the wall of the GI tract includes a hydrophilic substance suitable for facilitating sliding of the balloon against the wall of the GI tract.

For some applications, the balloon is shaped so as to define a proximal lobe and a distal lobe, the lobes being in fluid communication with each other.

There is yet additionally provided, in accordance with an embodiment of the present invention, apparatus for use with a biologically-compatible-fluid pressure source, including:

an elongate carrier, adapted to be inserted through a proximal opening of a body lumen; and a piston head coupled to a distal portion of the carrier and adapted to:

form a pressure seal with a wall of the lumen after the carrier has been inserted into the lumen, and be withdrawn proximally through the body lumen in response to pressure from the fluid pressure source.

In an embodiment, the lumen includes a gastrointestinal (GI) tract, and the piston head is adapted to form the pressure seal with the wall of the GI tract after the carrier has been inserted into the GI tract. In an embodiment, the GI tract includes a colon, and the piston head is adapted to form the pressure seal with the wall of the colon after the carrier has been inserted into the colon.

In an embodiment, the piston head is adapted to be in direct contact with the wall of the GI tract after the carrier has been inserted into the GI tract.

For some applications, an outer surface of the piston head forming the pressure seal with the wall of the GI tract includes a low friction coating suitable for facilitating sliding of the piston head against the wall of the GI tract.

For some applications, the piston head is shaped so as to define a proximal lobe and a distal lobe, the lobes being in fluid communication with each other.

For some applications, the apparatus includes a pressure-application tube in fluid communication with (a) a distal site within the GI tract distal to the piston head, and (b) the fluid pressure source, the tube adapted to introduce the pressure to the distal site.

For some applications, the apparatus includes:

a fluid source;

an image-capturing device, coupled to the carrier in a vicinity of a distal end of the carrier; and at least one fluid supply tube coupled to the carrier, the tube in fluid communication with the fluid source, and the distal end of the carrier is shaped so as to define one or more openings in fluid communication with the tube, the openings oriented so as to spray at least a portion of the image-capturing device when fluid is provided by the fluid source.

In an embodiment, the apparatus is adapted to facilitate passage of fluid out of the GI tract from a proximal site within the GI tract proximal to the piston head. For some applications, the apparatus includes a vent tube in fluid communication with the proximal site and outside the GI tract, the tube adapted to facilitate passage of fluid from the proximal site to the outside, so as to reduce a pressure at the proximal site. For some applications, the vent tube is adapted to passively permit the passage of the fluid from the proximal site. For some applications, the apparatus includes a suction source coupled to the vent tube, adapted to actively facilitate the passage of the fluid from the proximal site.

In an embodiment, the piston head is adapted to be inflated so as to form and maintain the pressure seal with the wall of the GI tract. For some applications, the apparatus includes a piston-head-pressure sensor, adapted to sense a pressure within the piston head. For some applications, the piston-head-pressure sensor is adapted to be disposed within the piston head. For some applications, the piston-head-pressure sensor is adapted to be disposed in a vicinity of the proximal opening of the GI tract. For some applications, the piston-head-pressure sensor is adapted to be disposed outside of the GI tract.

For some applications, the apparatus includes a distal pressure sensor, adapted to sense a pressure within the GI tract distal to the piston head. For some applications, the distal pressure sensor is adapted to be disposed distal to the piston head. For some applications, the distal pressure sensor is adapted to be disposed in a vicinity of the proximal opening of the GI tract. For some applications, the distal pressure sensor is adapted to be disposed outside of the GI tract.

For some applications, the apparatus includes a proximal pressure sensor, adapted to sense a pressure within the GI tract proximal to the piston head. For some applications, the proximal pressure sensor is adapted to be disposed in a vicinity of the piston head. For some applications, the proximal pressure sensor is adapted to be disposed in a vicinity of the proximal opening of the GI tract. For some applications, the proximal pressure sensor is adapted to be disposed outside of the GI tract.

For some applications, the apparatus includes a pressure sensor, adapted to measure a first pressure associated with operation of the apparatus; and a control unit, adapted to regulate a second pressure associated with operation of the apparatus responsive to the measurement of the pressure sensor. For some applications, the pressure sensor is adapted to measure a pressure selected from the list consisting of: a pressure distal to the piston head, a pressure proximal to the piston head, and a pressure within the piston head.

There is also provided, in accordance with an embodiment of the present invention, apparatus including:

an elongate carrier adapted to be inserted through a proximal opening of a body lumen;

an annular balloon, shaped so as to form an opening therethrough for insertion of the carrier, the balloon adapted to be at least partially inserted into the proximal opening, and to be expandable to form a pressure seal between the balloon and a wall of the body lumen in a vicinity of the proximal opening;

first and second fluid pressure sources;

a first tube, coupled between the first pressure source and an interior of the balloon; and a second tube, coupled between the second pressure source and an interior of the lumen distal to the annular balloon.

In an embodiment, the body lumen includes a colon, the proximal opening includes a rectum, and the balloon is adapted to be at least partially inserted into the rectum, and to be expandable to form the pressure seal between the balloon and the wall of the colon.

For some applications, at least one of the first and second pressure sources is adapted to be positioned outside the colon.

For some applications, the apparatus includes a ring coupled to the balloon, the ring adapted to abut against the rectum, and the ring shaped so as to form an opening therethrough for insertion of the carrier.

For some applications, the first pressure source includes a powered fluid pressure source. Alternatively, the first pressure source includes a manually-operated fluid pressure source. For some applications, the manually-operated pressure source includes a syringe.

There is further provided, in accordance with an embodiment of the present invention, apparatus including:

an elongate carrier, adapted to be inserted through a proximal opening of a body lumen; and an inflatable cuff, shaped so as to define an opening therethrough through which the carrier can be inserted, the cuff adapted to form a pressure seal with a wall of the body lumen when the cuff is in an inflated state in a vicinity of the proximal opening.

In an embodiment, the body lumen includes a colon, the proximal opening includes a rectum, and the carrier is adapted to be inserted through the rectum of the colon.

There is still further provided, in accordance with an embodiment of the present invention, apparatus for use with a fluid source, the apparatus including:

an elongate carrier, adapted to be inserted through a proximal opening of a body lumen;

an image-capturing device, fixed to the carrier in a vicinity of a distal end of the carrier; and at least one fluid supply tube coupled to the carrier, the tube in fluid communication with the fluid source, wherein the distal end of the carrier is shaped so as to define one or more openings in fluid communication with the tube, the openings oriented so as to spray at least a portion of the image-capturing device when fluid is provided by the fluid source.

In an embodiment, the body lumen includes a colon, and the carrier is adapted to be inserted through the proximal opening of the colon.

For some applications, the distal end of the carrier is shaped so as to define between 4 and 10 openings through which the fluid flows when provided by the fluid source. For some applications, the openings are disposed circumferentially about the distal end of the carrier. For some applications, the openings are positioned at a circumferential angle, so as to create a vortex around the image-capturing device when the fluid is provided by the fluid source.

For some applications, the image-capturing device includes an optical member that is shaped so as to define a lateral surface configured to provide omnidirectional lateral viewing, and the openings are oriented so as to spray at least a portion of the lateral surface of the optical member. For some applications, the optical member is shaped so as to define a forward surface configured to provide forward viewing, and the openings are oriented so as to spray at least a portion of the forward surface of the optical member.

There is additionally provided, in accordance with an embodiment of the present invention, apparatus for use in a body lumen having a proximal opening, the apparatus including:

an elongate carrier, adapted to be inserted through the proximal opening of the lumen;

an image-capturing device, fixed in a first vicinity of a distal end of the carrier, and adapted to provide omnidirectional lateral viewing; and an inflation element, fixed in a second vicinity of the distal end, and adapted to increase a diameter of the carrier in the second vicinity to an extent sufficient to position the image-capturing device a distance from a wall of the lumen sufficient to enable omnidirectional focusing of the image-capturing device.

In an embodiment, the lumen includes a gastrointestinal (GI) tract, and the carrier is adapted to be inserted through the proximal opening of the GI tract.

For some applications, the inflation element is adapted to increase the diameter of the carrier in the second vicinity such that the image-capturing device is at least 15 mm from the wall.

For some applications, the inflation element includes an expandable sponge. Alternatively or additionally, the inflation element includes a set of one or more rings, selected from the list consisting of: inflatable rings, and expandable rings. Further alternatively or additionally, the inflation element includes an inflatable balloon.

In an embodiment, the GI tract includes a colon, and the carrier is adapted to be inserted through the proximal opening of the colon. For some applications, the inflation element is adapted to increase the diameter of the carrier in the second vicinity to between 30 and 45 mm.

There is yet additionally provided, in accordance with an embodiment of the present invention, apparatus for use in a body lumen having a proximal opening, the apparatus including:

first and second fluid pressure sources;

an elongate carrier, adapted to be inserted through the proximal opening of the body lumen;

an inflatable piston head coupled to a distal portion of the carrier, and adapted to form a pressure seal with a wall of the lumen after the carrier has been inserted into the lumen;

a first passageway in fluid communication with the first pressure source and a proximal portion of the lumen proximal to the piston head;

a second passageway in fluid communication with the second pressure source and the piston head;

first and second pressure sensors, adapted to measure a first measurable pressure in the proximal portion of the lumen, and a second measurable pressure in the piston head, respectively; and a control unit, adapted to cause the piston head to be advanced distally in the lumen by:
 while the first pressure source applies a first applied pressure to the proximal portion of the lumen,
 regulating the second measurable pressure in the piston head to be equal to the first measurable pressure in the proximal portion of the lumen plus a positive value, by driving the second pressure source to apply a second applied pressure.

In an embodiment, the lumen includes a gastrointestinal (GI) tract, and the carrier is adapted to be inserted through the proximal opening of the GI tract. In an embodiment, the GI tract includes a colon, and the carrier is adapted to be inserted through the proximal opening of the colon.

In an embodiment, the piston is adapted to be in direct contact with the wall of the GI tract after the carrier has been inserted into the GI tract.

For some applications, the apparatus includes a third passageway in fluid communication with a portion of the GI tract distal to the piston head and a site outside the GI tract.

For some applications, the first passageway has a diameter of between 3 and 6 mm.

For some applications, the first pressure sensor is adapted to be disposed in a vicinity of the piston head. Alternatively, for some applications, the first pressure sensor is adapted to be disposed in a vicinity of the proximal opening of the GI tract. For some applications, the first pressure sensor is adapted to be disposed outside of the GI tract.

For some applications, the second pressure sensor is adapted to be disposed within the piston head. For some applications, the second pressure sensor is adapted to be disposed in a vicinity of the proximal opening of the GI tract. For some applications, the second pressure sensor is adapted to be disposed outside of the GI tract.

For some applications, the positive value is between 1 and 5 millibar. For some applications, the positive value is between 1.5 and 2.5 millibar.

For some applications, the control unit is adapted to set the second measurable pressure in the piston head at an initial value prior to application of the first applied pressure, by driving the second pressure source to apply the second applied pressure. For some applications, the initial value is between 5 and 15 millibar, and the control unit is adapted to set the second measurable pressure at between 5 and 15 millibar. For some applications, the control unit is adapted to regulate the second measurable pressure to be equal to the greater of: (a) the initial value, and (b) the first measurable pressure plus the positive value.

There is also provided, in accordance with an embodiment of the present invention, apparatus for use with a biologically-compatible-fluid pressure source, including:

an elongate carrier, adapted to be inserted through a proximal opening of a body lumen; and a distal piston head coupled to a distal portion of the carrier and adapted to:
 form a pressure seal with a wall of the lumen after the carrier has been inserted into the lumen, and
 be advanced distally through the body lumen in response to pressure from the fluid pressure source applied to an external surface of the distal piston head.

In an embodiment, the lumen includes a gastrointestinal (GI) tract, and the distal piston head is adapted to form the pressure seal with the wall of the GI tract after the carrier has been inserted into the GI tract. In an embodiment, the GI tract includes a colon, and the distal piston head is adapted to form the pressure seal with the wall of the colon after the carrier has been inserted into the colon.

In an embodiment, the distal piston head is adapted to be in direct contact with the wall of the GI tract after the carrier has been inserted into the GI tract.

For some applications, an outer surface of the distal piston head forming the pressure seal with the wall of the GI tract includes a low friction coating suitable for facilitating sliding of the distal piston head against the wall of the GI tract.

For some applications, the apparatus includes:

a fluid source;

an optical member coupled in a vicinity of the distal portion of the carrier; and at least one fluid supply tube coupled to the carrier, the tube in fluid communication with the fluid source, and the distal portion of the carrier is shaped so as to define one or more openings in fluid communication with the tube, the openings oriented so as to spray at least a portion of the optical member when fluid is provided by the fluid source.

For some applications, the apparatus includes:

an optical system including an optical member configured to provide omnidirectional lateral viewing; and an inflation element, fixed in a vicinity of the distal portion of the carrier, and adapted to increase a diameter of the carrier in the vicinity to an extent sufficient to position the optical member a distance from the wall sufficient to enable omnidirectional focusing of the optical system.

In an embodiment, the apparatus is adapted to facilitate distal advancement of the distal piston head by facilitating passage of fluid out of the GI tract from a distal site within the GI tract distal to the distal piston head. For some applications, the apparatus is adapted to facilitate the passage of an amount of the fluid out of the GI tract from the distal site sufficient to maintain a pressure of less than 10 millibar at the distal site. For some applications, the apparatus is adapted to facilitate the passage of at least 100 cc of the fluid out of the GI tract from the distal site, per minute that the distal piston head advances distally. For some applications, the apparatus is adapted to facilitate the passage of at least 300 cc of the fluid out of the GI tract from the distal site, per minute that the distal piston head advances distally.

For some applications, the apparatus is adapted to facilitate the passage of at least 3 cc of the fluid out of the GI tract from the distal site, per centimeter that the distal piston head advances distally. For some applications, the apparatus is adapted to facilitate the passage of at least 10 cc of the fluid out of the GI tract from the distal site, per centimeter that the distal piston head advances distally.

For some applications, the apparatus includes a vent tube, and the apparatus is adapted to facilitate the passage of the fluid out of the GI tract from the distal site within the GI tract through the vent tube. For some applications, the vent tube is shaped to define an inner diameter thereof that is between 1 and 3 millimeters. For some applications, the vent tube is adapted to passively permit the passage of the fluid out of the GI tract from the distal site within the GI tract.

For some applications, the vent tube is adapted to be coupled to a suction source, whereby to actively facilitate the passage of the fluid out of the GI tract from the distal site within the GI tract. For some applications, the vent tube is adapted to be coupled to the suction source such that during operation of the apparatus, a pressure distal to the distal piston head is between −5 millibar and +15 millibar.

For some applications, the apparatus includes a suction source coupled to the vent tube, adapted to actively facilitate the passage of the fluid out of the GI tract from the distal site within the GI tract. For some applications, the suction source is adapted to maintain a pressure distal to the distal piston head is between −5 millibar and +15 millibar.

For some applications, the distal piston head is adapted to be inflated so as to form and maintain the pressure seal with the wall of the GI tract, and the distal piston head is adapted to be intermittently deflated at least in part, while in the GI tract, whereby to facilitate the passage of the fluid out of the GI tract from the site within the GI tract distal to the distal piston head.

In an embodiment, the distal piston head is adapted to be inflated so as to form and maintain the pressure seal with the wall of the GI tract. For some applications, the apparatus includes an auxiliary piston head, coupled to the carrier at a position proximal to the distal piston head; the auxiliary piston head is adapted to be inflated so as to form and maintain an auxiliary pressure seal with the wall of the GI tract; and (a) at at least one time while the carrier is within the GI tract, the distal piston head is adapted to be in a state of being already deflated at least in part, simultaneously with the auxiliary piston head being already inflated and being advanced distally through the GI tract in response to pressure from the fluid pressure source, and (b) at at least one other time while the carrier is within the GI tract, the auxiliary piston head is adapted to be in a state of being already deflated at least in part, simultaneously with the distal piston head being already inflated and being advanced distally through the GI tract in response to pressure from the fluid pressure source.

For some applications, the apparatus includes a piston-head-pressure sensor, adapted to sense a pressure within the distal piston head. For some applications, the piston-head-pressure sensor is adapted to be disposed within the distal piston head. For some applications, the piston-head-pressure sensor is adapted to be disposed in a vicinity of the proximal opening of the GI tract. For some applications, the piston-head-pressure sensor is adapted to be disposed outside of the GI tract. For some applications, the apparatus includes a distal pressure sensor, adapted to sense a pressure within the GI tract distal to the distal piston head. For some applications, the distal pressure sensor is adapted to be disposed distal to the distal piston head. Alternatively, for some applications, the distal pressure sensor is adapted to be disposed in a vicinity of the proximal opening of the GI tract. For some applications, the distal pressure sensor is adapted to be disposed outside of the GI tract.

For some applications, the apparatus includes a proximal pressure sensor, adapted to sense a first measurable pressure, within a proximal portion of the GI tract proximal to the distal piston head. For some applications, the apparatus includes a distal pressure sensor, adapted to sense a pressure distal to the distal piston head. For some applications, the proximal pressure sensor is adapted to be disposed in a vicinity of the distal piston head.

For some applications, the proximal pressure sensor is adapted to be disposed in a vicinity of the proximal opening of the GI tract. For some applications, the proximal pressure sensor is adapted to be disposed outside of the GI tract. For some applications, the apparatus includes a piston-head-pressure sensor, adapted to sense a second measurable pressure, within the distal piston head. For some applications, the pressure source includes a first pressure source, adapted to apply a first applied pressure to the proximal portion of the GI tract, and the apparatus includes:
 a second pressure source, adapted to apply a second applied pressure to an interior of the distal piston head; and
 a control unit, adapted to advance the distal piston head distally in the GI tract by:
  while the first pressure source applies the first applied pressure to the proximal portion,
  regulating the second measurable pressure in the distal piston head to be equal to the first measurable pressure in the proximal portion of the GI tract plus a positive value, by driving the second pressure source to apply the second applied pressure.

For some applications, the apparatus includes a pressure sensor, adapted to measure a first pressure associated with operation of the apparatus; and a control unit, adapted to regulate a second pressure associated with operation of the apparatus responsive to the measurement of the pressure sensor. For some applications, the pressure sensor is adapted to measure a pressure selected from the list consisting of: a pressure distal to the distal piston head, a pressure proximal to the distal piston head, and a pressure within the distal piston head. For some applications, the control unit is adapted to regulate the pressure being measured by the pressure sensor. For some applications, the control unit is adapted to regulate a pressure other than that being measured by the pressure sensor.

For some applications, the distal piston head is shaped to define a proximal lobe and a distal lobe, the lobes being in fluid communication with each other.

For some applications, a volume of a first one of the lobes is adapted to decrease in response to a constriction of the GI tract adjacent thereto, a volume of a second one of the lobes is adapted to remain constant in the absence of a change in GI tract diameter adjacent thereto, even if the volume of the first lobe is decreased, and a pressure within the first and second lobes is equal in steady state, regardless of the decrease in volume of the first lobe.

For some applications, the distal piston head is adapted to be at an inflation pressure between 10 and 60 millibar during advancement through the GI tract. For some applications, the distal piston head is adapted to advance through the GI tract in response to a pressure from the fluid pressure source that is between 30% and 100% of the inflation pressure. For some applications, the distal piston head is adapted to advance through the GI tract in response to a pressure from the fluid pressure source that is between 50% and 100% of the inflation pressure.

For some applications, the distal piston head is adapted to be at an inflation pressure between 20 and 50 millibar during advancement through the GI tract. For some applications, the distal piston head is adapted to be at an inflation pressure between 30 and 45 millibar during advancement through the GI tract. For some applications, the distal piston head is adapted to advance through the GI tract in response to a pressure from the fluid pressure source that is between 30% and 100% of the inflation pressure. For some applications, the distal piston head is adapted to advance through the GI tract in response to a pressure from the fluid pressure source that is between 50% and 100% of the inflation pressure. For some applications, the distal piston head is adapted to advance through the GI tract in response to a pressure from the fluid pressure source that is between 50% and 80% of the inflation pressure.

For some applications, the distal piston head is shaped to define a distally-narrowing portion, and is adapted to be inserted into the GI tract such that a tip of the distally-narrowing portion points in a distal direction when the distal piston head is in the GI tract. For some applications, a proximal base of the distally-narrowing portion has a characteristic fully-inflated diameter that is larger than a diameter of at least a part of the GI tract through which the distally-narrowing portion is adapted to pass, whereby the base of the distally-narrowing portion does not inflate fully when the base is in that part of the GI tract.

There is further provided, in accordance with an embodiment of the present invention, apparatus for use in a body lumen having a proximal opening, the apparatus including:

an elongate carrier, adapted to be inserted through the proximal opening of the body lumen;

an inflatable piston head coupled to a distal portion of the carrier, and adapted to form a pressure seal with a wall of the lumen after the carrier has been inserted into the lumen; and a biologically-compatible fluid proximal pressure source, adapted to be in fluid communication with a proximal portion of the lumen proximal to the piston head, and to apply pressure sufficient to advance the carrier distally through the body lumen.

In an embodiment, the lumen includes a gastrointestinal (GI) tract, and the piston head is adapted to form the pressure seal with the wall of the GI tract. In an embodiment, the GI tract includes a colon, and the piston head is adapted to form the pressure seal with the wall of the colon.

In an embodiment, the piston head is adapted to be in direct contact with the wall of the GI tract.

For some applications, the apparatus includes a first passageway, and the proximal pressure source is in the fluid communication with the proximal portion of the GI tract via the first passageway.

For some applications, the apparatus includes a piston pressure source, adapted to be in fluid communication with the piston head, and to apply pressure to the piston head in order to inflate the piston head.

For some applications, the apparatus includes a second passageway, and the piston pressure source is in the fluid communication with the piston head via the second passageway.

For some applications, the apparatus includes a proximal pressure sensor, adapted to measure a pressure in the proximal portion of the GI tract; and a piston pressure sensor, adapted to measure a pressure in the piston head.

For some applications, the apparatus includes a proximal pressure sensor, adapted to measure a pressure in the proximal portion of the GI tract. For some applications, the proximal pressure sensor is adapted to be disposed in a vicinity of the piston head. Alternatively, for some applications, the proximal pressure sensor is adapted to be disposed in a vicinity of the proximal opening of the GI tract. For some applications, the proximal pressure sensor is adapted to be disposed outside of the GI tract.

For some applications, the apparatus includes a piston pressure sensor, adapted to measure a pressure in the piston head. For some applications, the piston pressure sensor is adapted to be disposed within the piston head. For some applications, the piston pressure sensor is adapted to be disposed in a vicinity of the proximal opening of the GI tract. For some applications, the piston pressure sensor is adapted to be disposed outside of the GI tract.

For some applications, the apparatus includes a vent tube, adapted to be in fluid communication with a distal portion of the GI tract distal to the piston head, and with outside of the GI tract, and to facilitate distal advancement of the piston head by facilitating passage of fluid out of the GI tract from the distal portion. For some applications, the apparatus includes a distal pressure sensor, adapted to measure a pressure in the distal portion of the GI tract. For some applications, the distal pressure sensor is adapted to be disposed distal to the piston head. For some applications, the distal pressure sensor is adapted to be disposed in a vicinity of the proximal opening of the GI tract. For some applications, the distal pressure sensor is adapted to be disposed outside of the GI tract.

For some applications, the apparatus is adapted to facilitate the passage of an amount of the fluid out of the GI tract from the distal portion sufficient to maintain a pressure of less than 10 millibar at the distal portion.

For some applications, the vent tube is adapted to passively permit the passage of the fluid out of the GI tract from the distal portion.

For some applications, the apparatus includes a suction source coupled to the vent tube, adapted to actively facilitate the passage of the fluid out of the GI tract from the distal portion.

For some applications, the apparatus is adapted to facilitate the passage of at least 100 cc of the fluid out of the GI tract from the distal portion, per minute that the piston head advances distally. For some applications, the apparatus is adapted to facilitate the passage of at least 300 cc of the fluid out of the GI tract from the distal portion, per minute that the piston head advances distally.

For some applications, the apparatus is adapted to facilitate the passage of at least 3 cc of the fluid out of the GI tract from the distal portion, per centimeter that the piston head advances distally. For some applications, the apparatus is adapted to facilitate the passage of at least 10 cc of the fluid out of the GI tract from the distal portion, per centimeter that the piston head advances distally.

There is still further provided, in accordance with an embodiment of the present invention, apparatus for use in a body lumen having a proximal opening, the apparatus including:

an elongate carrier, adapted to be inserted through the proximal opening of the body lumen;

an inflatable piston head coupled to a distal portion of the carrier, and adapted to form a pressure seal with a wall of the lumen after the carrier has been inserted into the lumen;

a biologically-compatible fluid proximal pressure source, adapted to be in fluid communication with a proximal portion of the lumen proximal to the piston head, and to apply pressure sufficient to advance the carrier distally through the body lumen; and a piston head pressure sensor, adapted to sense a piston head pressure in the piston head, the piston head pressure sensor disposed in a vicinity of the proximal opening of the lumen, and in fluid communication with an interior of the piston head.

In an embodiment, the lumen includes a gastrointestinal (GI) tract, and the piston head is adapted to form the pressure seal with the wall of the GI tract. In an embodiment, the GI tract includes a colon, and the piston head is adapted to form the pressure seal with the wall of the colon.

In an embodiment, the piston head is adapted to be in direct contact with the wall of the GI tract.

For some applications, the piston head pressure sensor is adapted to be in fluid communication with the interior of the piston head via a passageway, a proximal end of which is disposed in the vicinity of the proximal opening of the GI tract.

For some applications, the piston head pressure sensor is adapted to be disposed outside of the GI tract.

For some applications, the apparatus includes a biologically-compatible fluid piston head pressure source, adapted to be in fluid communication with the interior of the piston head via a passageway, and the piston head pressure sensor is adapted to be in fluid communication with the interior of the piston head via the passageway.

For some applications, the apparatus includes a proximal portion pressure sensor, adapted to sense a proximal portion pressure in the proximal portion of the GI tract, and disposed in a vicinity of the proximal opening of the GI tract. For some applications, the proximal portion pressure sensor is adapted to be disposed outside of the GI tract.

For some applications, the apparatus includes a distal portion pressure sensor, adapted to sense a distal portion pressure in a distal portion of the GI tract distal to the piston head, and disposed in a vicinity of the proximal opening of the GI tract. For some applications, the distal portion pressure sensor is adapted to be disposed outside of the GI tract.

There is additionally provided, in accordance with an embodiment of the present invention, a method including:

forming a pressure seal between a piston head and a wall of a body lumen;

advancing the piston head distally through the body lumen by:

applying fluid pressure to an external surface of the piston head, and facilitating passage of fluid out of the lumen from a site within the lumen distal to the piston head; and providing omnidirectional lateral viewing from a vicinity of the piston head.

There is yet additionally provided, in accordance with an embodiment of the present invention, a method including:

forming a pressure seal between a wall of a body lumen and a piston head shaped so as to define a proximal lobe and a distal lobe in fluid communication with each other; and advancing the piston head distally through the body lumen by applying fluid pressure to an external surface of the piston head.

There is also provided, in accordance with an embodiment of the present invention, a method including:

providing an elongate carrier having a balloon coupled to a distal portion thereof, the balloon having a hydrophilic substance disposed at an external surface thereof, and inserting the elongate carrier through a proximal opening of a body lumen, such that the balloon comes in direct contact with a wall of the lumen.

There is further provided, in accordance with an embodiment of the present invention, a method including:

providing an elongate carrier having a balloon coupled to a distal portion thereof, an outer surface of the balloon having a low friction coating suitable for facilitating sliding of the balloon against the wall of the lumen; and inserting the elongate carrier through a proximal opening of a body lumen, such that the outer surface of the balloon comes in direct contact with a wall of the lumen.

There is still further provided, in accordance with an embodiment of the present invention, a method including:

providing an elongate carrier having a balloon coupled to a distal portion thereof, the balloon having a characteristic thickness of no more than 20 microns; and inserting the elongate carrier through a proximal opening of a body lumen, such that the balloon comes in direct contact with a wall of the lumen.

There is additionally provided, in accordance with an embodiment of the present invention, a method including:

forming a pressure seal between a piston head and a wall of a body lumen; and applying fluid pressure to an external surface of the piston head to withdraw the piston head proximally through the body lumen.

There is yet additionally provided, in accordance with an embodiment of the present invention, a method including:

inserting an annular balloon at least partially into a proximal opening of a body lumen;

expanding the balloon to form a seal between the balloon and a wall of the body lumen in a vicinity of the proximal opening;

inserting an elongate carrier into the lumen through an opening that passes through the balloon; and applying pressure to an interior of the lumen distal to the balloon.

There is also provided, in accordance with an embodiment of the present invention, a method including:

inserting an inflatable cuff at least partially into a proximal opening of a body lumen;

inflating the cuff to form a seal with a wall of the body lumen in a vicinity of the proximal opening; and inserting an elongate carrier into the lumen through an opening that passes through the cuff.

There is further provided, in accordance with an embodiment of the present invention, a method including:

inserting, through a proximal opening of a body lumen, an elongate carrier having an image-capturing device fixed thereto in a vicinity of a distal end thereof; and spraying, from one or more openings in the distal end of the carrier, fluid onto at least a portion of the image-capturing device.

There is still further provided, in accordance with an embodiment of the present invention, a method including:

inserting, through a proximal opening of a body lumen, an elongate carrier having an image-capturing device fixed thereto in a first vicinity of a distal end of the carrier, for providing omnidirectional lateral viewing; and increasing a diameter of the carrier in a second vicinity of the distal end to an extent sufficient to position the image-capturing device a distance from a wall of the lumen sufficient to enable omnidirectional focusing of the image-capturing device.

There is additionally provided, in accordance with an embodiment of the present invention, a method including:

forming a pressure seal between an inflatable piston head and a wall of a body lumen;

measuring a first measurable pressure in a proximal portion of the lumen proximal to the piston head, and a second measurable pressure in the piston head; and advancing the piston head distally through the lumen by:
applying a first applied pressure to the proximal portion of the lumen, and
regulating the second measurable pressure in the piston head to be equal to the first measurable pressure in the proximal portion of the lumen plus a positive value, by applying a second applied pressure to piston head.

There is yet additionally provided, in accordance with an embodiment of the present invention, a method including:

forming a pressure seal between a distal piston head and a wall of a body lumen; and applying fluid pressure to an external surface of the distal piston head to advance the piston head distally through the lumen.

There is also provided, in accordance with an embodiment of the present invention, a method including:

forming a pressure seal between a piston head and a wall of a body lumen;

applying fluid pressure to an external surface of the distal piston head to advance the piston head distally through the lumen; and sensing, at a vicinity of a proximal opening of the lumen, a piston head pressure in the piston head.

BRIEF DESCRIPTION OF THE DRAWINGS

The present invention will be understood and appreciated more fully from the following detailed description taken in conjunction with the drawings in which:

FIG. 1 is a simplified pictorial illustration of a system, constructed and operative in accordance with an embodiment of the present invention, which may be suitable for imaging body lumens, such as the GI tract;

FIGS. 2 and 3 are simplified sectional illustrations of distal and proximal portions, respectively, of the system of FIG. 1;

FIG. 12 is a schematic cross-sectional illustration of an optical system, in accordance with an embodiment of the present invention;

FIGS. 13A and 13B are pictorial illustrations of another system for use in a body lumen, in accordance with an embodiment of the present invention;

DETAILED DESCRIPTION OF EMBODIMENTS

Figure 3:
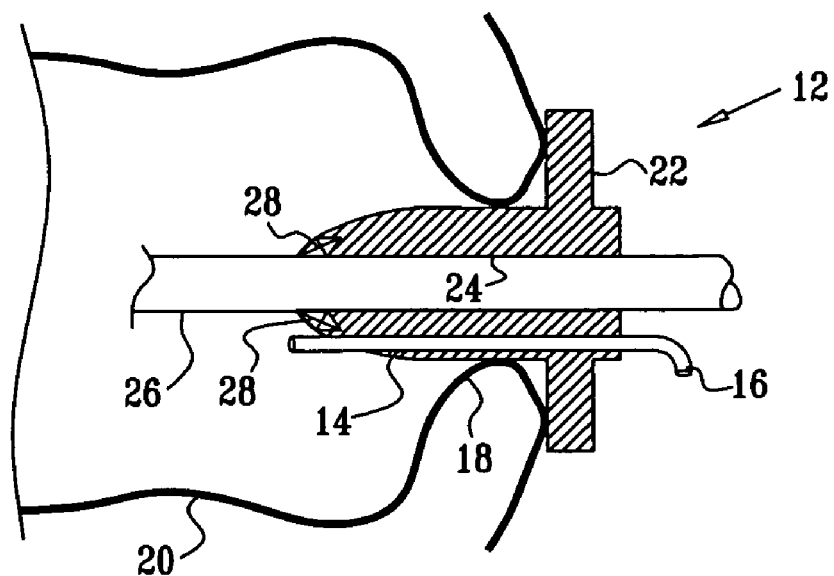
Figure 4:
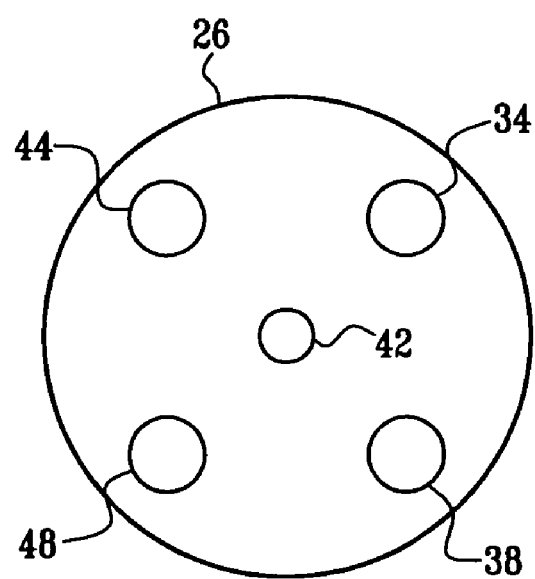
FIG. 4 is a simplified sectional illustration of a carrier of the system of FIG. 1, the section being taken transverse to a longitudinal axis of the carrier, in accordance with an embodiment of the present invention.

Reference is now made to FIGS. 1-3, which illustrate a system 10, constructed and operative in accordance with an embodiment of the present invention.

As seen best in FIG. 3, system 10 may include a guide member 12, which may be constructed of any medically safe material, such as but not limited to, plastic or metal. Guide member 12 may be formed with a first passageway 14 connected to a source 16 of a pressurized biologically-compatible fluid ("fluid pressure source 16"), such as but not limited to, a source of pressurized air, $CO_2$ or water. Guide member 12 may be at least partially insertable into a proximal opening 18 (e.g., the rectum) of a body lumen 20 (e.g., the colon). Guide member 12 may include an annular ring 22 for abutting against the proximal opening 18.

Guide member 12 may be formed with a bore 24 through which an elongate carrier 26 may be arranged for sliding movement. An O-ring 28 may be provided for dynamically sealing carrier 26 in its sliding motion relative to the guide member 12. Carrier 26 may be any slender wire, catheter or tube and the like, constructed of any medically safe material, such as but not limited to, a flexible plastic or metal. Carrier 26, including its tip, may be safely deflected and steered through body lumen 20.

In an embodiment of the present invention, guide member 12 comprises a microcuff, which forms a seal with the wall of lumen 20, in order to maintain positive pressure within lumen 20. For example, the microcuff may comprise a cuff manufactured by Microcuff GmbH (Weinheim, Germany), and/or described in the above-mentioned PCT Publication WO 04/069057, U.S. Patent Application Publication 2003/0000526, and/or PCT Publication WO 03/045487. The creation of such positive pressure is described hereinbelow.

A piston head 30 may be mounted on carrier 26. Piston head 30 may be inflatable, and as such may be constructed of any medically safe elastomeric material, such as but not limited to, a bladder or membrane made of polyurethane or silicone rubber, for example. An image-capturing device 32 may be mounted on carrier 26 distal to piston head 30. Piston head 30 is typically fixed to carrier 26 and sealed thereto with O-rings 33, but optionally may be arranged to slide on carrier 26 up to some distal stop which arrests further distal motion of piston head 30 (image-capturing device 32 may serve as the distal stop, for example). Image-capturing device 32 may comprise, without limitation, a camera (e.g., CCD or CMOS), or alternatively x-ray, ultrasonic, MRI, infrared and/or microwave imaging devices.

Other therapeutic or diagnostic devices may be mounted on or in carrier 26, such as but not limited to, a magnet, drug delivery devices (e.g., via iontophoresis), gene therapy devices and others.

Carrier 26 may include a second passageway 34 in fluid communication with piston head 30, connected to a source of fluid pressure 36 (e.g., pressurized air or water) for inflating piston head 30. For some applications, piston head-inflation fluid pressure source 36 is regulated to maintain a generally constant pressure within piston head 30, regardless of changes of volume of the piston head which occur in response to diameter changes of lumen 20.

A vent tube 38 may pass through or around piston head 30, having an opening 40 distal to piston head 30 through which fluid is ventable to the outside. That is, the proximal end of vent tube 38 vents the fluid past guide member 12 to the outside. For some applications, the proximal end of vent tube 38 may be connected to a suction source (not shown) for sucking fluid through vent tube 38. "Fluid," as used herein, including in the claims, includes liquids and gases.

In an embodiment, vent tube 38 is not used, but instead piston head 30 is temporarily deflated (at least in part), intermittently and/or in response to excess pressure accumulating distal to piston head 30. The temporary deflation of the piston head allows venting of the distal pressure to occur through passageway 14, typically in conjunction with a temporary decoupling of passageway 14 from fluid pressure source 16.

A power supply tube 42 (e.g., containing electrical wires, fiber optics, etc.) may pass through carrier 26, for connection to image-capturing device 32. Alternatively, the electrical and optical components of image-capturing device 32 may have their own internal power source, with no need for external wiring. Image-capturing device 32 may wirelessly transmit or receive data to or from an external processor (not shown). The components of system 10 may be fully automated with sensors and operate in a closed or open control loop.

A fluid supply tube 44 may pass through carrier 26, which may be connected to a fluid source (not shown), e.g., pressurized water, for cleaning the area near image-capturing device 32, or in combination with the vent tube 38, for cleaning body lumen 20 itself (e.g., the colon).

Experiments carried out by the inventors have shown that the system, as described hereinabove, is able to safely and efficiently advance a colonoscope or other tool through the colon of an anesthetized 90 kg pig. In these experiments, elongate carrier 26 was generally radio-opaque, and its motion was tracked in real-time using fluoroscopic imaging. Vent tube 38 was utilized, having an inner diameter of 2 mm. It acted passively (without being connected to a suction source), in order to allow pressure accumulating distal to piston head 30 to be vented to the outside.

In these experiments, a range of operating pressures were examined. The proximal pressure and the pressure within the piston head (intra-head pressure) were controlled, and values were recorded at which satisfactory movement of piston head 30 was observed. In general, for intra-head pressures ranging between 25 and 40 millibar, movement of piston head 30 was observed when the proximal pressure reached 30-100% of the intra-head pressure.

Typically, when the proximal pressure was below a threshold value, no movement was observed. As the proximal pressure was elevated above the threshold value, piston head 30 advanced through the colon. If the proximal pressure increased significantly above the threshold pressure (e.g., 2-10 millibar above the threshold pressure), then there was pressure leakage between piston head 30 and the wall of lumen 20, and advancement of piston head 30 ceased. In response to such a leak, the proximal pressure was lowered, vent tube 38 allowed the excess accumulated distal pressure to vent to the outside, and movement of piston head 30 recommenced.

In an experiment, an inflatable piston head was formed of thin silicone, and was shaped to have a distal lobe, a proximal lobe, and an intermediate portion connecting the distal and proximal lobes. (See FIGS. 10A and 10B.) For an intra-head pressure of 30 millibar, the piston head advanced through the colon when the proximal pressure was maintained between 10 and 20 millibar. During advancement of the piston head, vent tube 38 vented to the outside the pressure that accumulated due to the advancement of the piston head. Leakage around the piston head was observed for proximal pressures greater than about 20 millibar. For an intra-head pressure of 40 millibar, the piston head advanced through the colon when the proximal pressure was maintained between 27 and 30 millibar, both on straight and curved portions of the colon. For straight portions of the colon, proximal pressures of as low as 20 millibar were also sufficient to produce satisfactory movement of the piston head.

Although the rate of advance of the two-lobed piston head was found to vary with the selected pressures, in one experiment using a thin-walled two-lobed piston head, a total time of 2 minutes passed during the advancing of a colonoscope 1.5 meters into the colon of the pig. In another experiment, using a thick-walled two-lobed piston head, an intra-head pressure of 70 millibar and proximal pressure of 50 millibar resulted in 1.5 meters of colonoscope advancement in 1 minute 41 seconds. Thin-walled piston heads useful for these embodiments of the invention typically have a head wall thickness between 10 and 100 microns, e.g., 50 microns or less than 20 microns, or a head wall thickness of less than 10 microns. Thick-walled piston heads useful for these embodiments of the invention typically have a head wall thickness greater than 100 microns, e.g., 150 microns, or 250 microns.

In another experiment, the piston head was formed of polyurethane, and was shaped like a cone, as described hereinbelow with reference to FIGS. 7-9. In this experiment, satisfactory advancement of the piston head was obtained at a proximal pressure of 35 millibar, when the intra-head pressure was also 35 millibar. The satisfactory advancement was obtained both on straight and curved portions of the colon.

It is noted that in these experiments, during the time when the intra-head pressure was kept constant, the volume of the piston head changed actively in response to changes in diameter of lumen 20.

Reference is now made to FIGS. 1, 2 and 5A-C, which illustrate operation of system 10, in accordance with an embodiment of the present invention. In this embodiment, an auxiliary piston head 46 may be mounted on the carrier proximal to distal piston head 30. Auxiliary piston head 46, which like piston head 30 may be inflatable, may be fixed axially to carrier 26 at a fixed distance from piston head 30. Auxiliary piston head 46 may be sealed with respect to carrier 26 with O-rings 47. Carrier 26 may include a third passageway 48 in fluid communication with auxiliary piston head 46, connected to a source of fluid pressure 50 for inflating auxiliary piston head 46.

System 10 may be inserted in the rectum with piston heads 30 and 46 initially deflated to facilitate insertion. Distal piston head 30 may then be gently inflated until it expands to the inner wall of body lumen 20. This configuration is shown in FIG. 1. Pressurized fluid (e.g., air) from fluid pressure source 16 may be introduced into the colon through the first passageway 14 of guide member 12. The pressurized fluid creates greater fluid pressure acting on the proximal side of piston head 30 than on the distal side of piston head 30. Opening 40 of vent tube 38 may assist in creating the pressure difference across piston head 30, either passively, or actively via applied suction. This pressure difference propels piston head 30 together with carrier 26 distally into the body lumen (in this example, the colon), as indicated by arrow 60. Image-capturing device 32 may capture images of body lumen 20 as system 10 travels therethrough.

In an embodiment of the present invention, the techniques described herein for propulsion by creating a pressure difference are applied in a reverse manner to actively propel piston head 30 together with carrier 26 proximally, i.e., to withdraw system 10 from lumen 20. Pressurized fluid (e.g., air) from a fluid pressure source is introduced to the distal side of piston head 30, via a pressure-application tube passing through or around piston head 30. Optionally, vent tube 38 serves as the pressure-application tube during withdrawal. The pressurized fluid creates greater fluid pressure acting on the distal side of piston head 30 than on the proximal side of piston head 30, thereby proximally propelling the piston head and the carrier. A vent tube between the proximal side of piston head 30 and outside the lumen may assist in creating the pressure difference across piston head 30, either passively, or actively via applied suction. Optionally, passageway 14 serves as the vent tube during withdrawal.

Figure 5A:
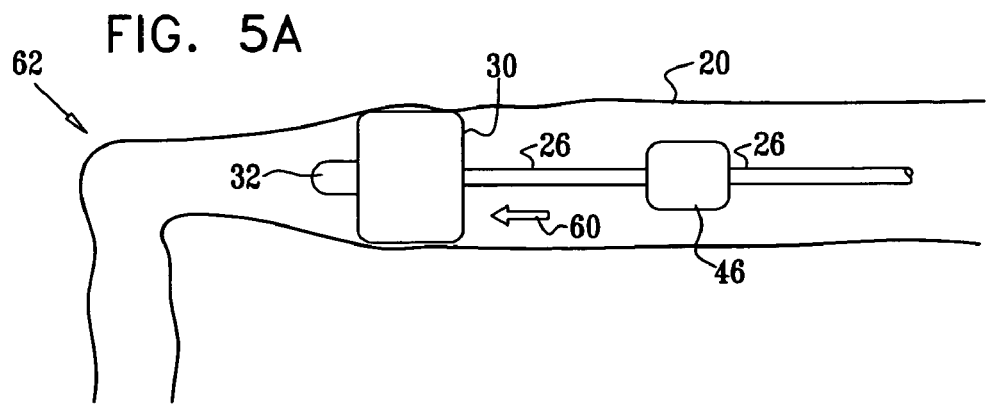
FIGS. 5A, 5B and 5C are simplified pictorial illustrations of the system of FIG. 1, showing three steps of a mode of operation thereof, wherein inflatable piston heads are inflated and deflated to negotiate obstacles in a body lumen, in accordance with an embodiment of the present invention.
Figure 5B:
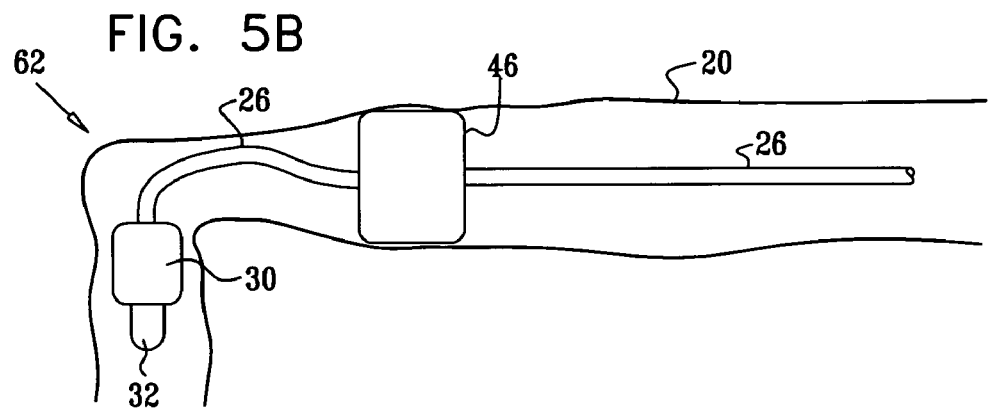
Figure 5C:
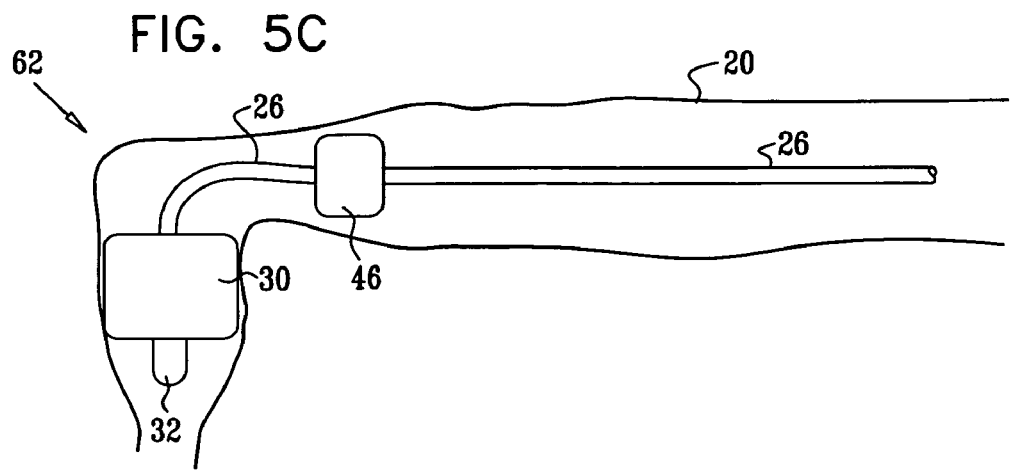

As seen in FIG. 5A, system 10 may eventually reach an obstacle or tight turn, indicated by arrow 62. In such a case, proximal piston head 46 may be inflated and distal piston head 30 may be deflated as shown in FIG. 5B. In this configuration, the pressurized fluid creates greater fluid pressure acting on the proximal side of proximal piston head 46 than on the distal side of proximal piston head 46. This pressure difference propels proximal piston head 46 together with carrier 26 distally, as indicated by arrow 64. This distal movement brings distal deflated piston head 30 past the obstacle, as seen in FIG. 5B. System 10 continues its distal movement in body lumen 20 until proximal piston head 46 reaches the obstacle. At this point, distal piston head 30 may be inflated and proximal piston head 46 may be deflated once again, as shown in FIG. 5C. Once again, the pressurized fluid creates greater fluid pressure acting on the proximal side of distal piston head 30 than on the distal side of distal piston head 30. The pressure difference propels system 10 distally in body lumen 20, and brings proximal deflated piston head 46 past the obstacle. The cycle may be repeated as often as necessary.

Figure 6:
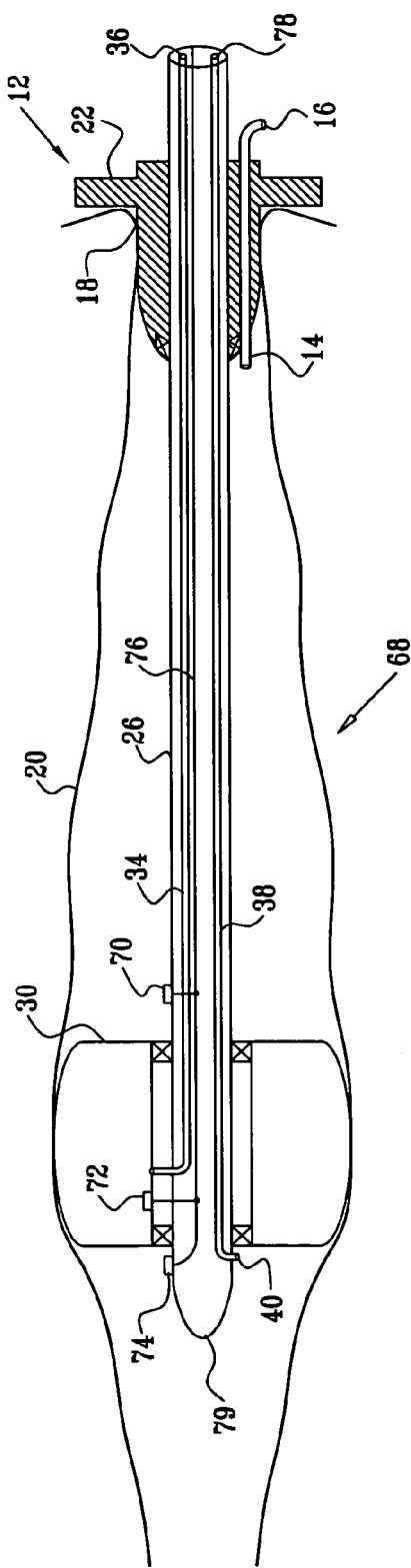
FIG. 6 is a pictorial illustration of a system for use in a body lumen, constructed and operative in accordance with an embodiment of the present invention.

Reference is now made to FIG. 6, which illustrates a system 68, constructed and operative in accordance with an embodiment of the present invention. System 68 operates in substantially the same manner as system 10, described hereinabove with reference to FIGS. 1-4, in that distal piston head 30 is inflated until it is in contact with body lumen 20, such that a seal between piston head 30 and lumen 20 is formed. Pressurized fluid is then introduced via first passageway 14, producing a larger pressure on the proximal face of piston head 30 than on the distal face of piston head 30, resulting in a net force acting to move piston head 30 distally. A sufficient net pressure force results in distal movement of piston head 30 along with elongate carrier 26 and a tool 79. Tool 79 may comprise an imaging device, a biopsy device, or other apparatus to be used in body lumen 20.

Additionally, for some applications of the present invention, a suction source 78 is coupled to opening 40 via vent tube 38 to provide suction on the distal face of piston head 30 and facilitate the distal movement of piston head 30. Providing suction at opening 40 may also be used in some applications to remove contents of the lumen, such as excess fluid or stool, that are impeding the movement of piston head 30. For some applications, the suction decreases an accumulation of gas distal to piston head 30 that may be uncomfortable for the patient.

System 68 typically comprises one or more pressure sensors, for example in order to be able to improve or optimize the performance of the system with respect to ease and speed of movement of system 68 through lumen 20. In particular, system 68 typically comprises one or more of the following pressure sensors:

a first pressure sensor 70, adapted to determine the pressure acting on the proximal face of distal piston 30;

a second pressure sensor 72, adapted to determine the inflation pressure of the distal piston head; and/or a third pressure sensor 74, adapted to determine the pressure acting on the distal face of piston head 30.

For some applications, the three pressure sensors are coupled to a pressure sensor bus 76, such that the various pressure readings can be sent to an electromechanical or mechanical control unit (not shown), which regulates the different pressures, either automatically or with input from the operator of the system. For some applications, only one of the pressure sensors is included in system 68 (e.g., sensor 70, sensor 72, or sensor 74). For other applications, two of the pressure sensors are included, and one is omitted (e.g., sensor 70, sensor 72, or sensor 74).

For some applications, first pressure sensor 70 is located proximal to distal piston head 30 in a vicinity of the piston head. Alternatively, first pressure sensor 70 is located in a vicinity of fluid pressure source 16, typically outside the body of the patient. In this latter configuration: (a) first pressure sensor 70 is integrated with pressure source 16, or is positioned separately from pressure source 16; and (b) first pressure sensor 70 is in fluid communication with a proximal portion of lumen 20 proximal to piston head 30, either via first passageway 14, or via a separate passageway in fluid communication with first pressure sensor 70 and the proximal portion of lumen 20 (separate passageway not shown). A distal end of such separate passageway is adapted to be positioned in the proximal portion of lumen 20, either in a vicinity of guide member 12, or more distally in lumen 20, such as in a vicinity of piston head 30 proximal to the piston head.

For some applications, second pressure sensor 72 is located inside distal piston head 30. Alternatively, second pressure sensor 72 is located in a vicinity of fluid pressure source 36, typically outside the body of the patient. In this latter configuration, second pressure sensor 72 is in fluid communication with piston head 30, either via second passageway 34, or via a separate passageway in fluid communication with second pressure sensor 72 and piston head 30 (separate passageway not shown).

For some applications, third pressure sensor 74 is located distal to distal piston head 30. Alternatively, third pressure sensor 74 is located in a vicinity of a proximal opening of vent tube 38 (which, for applications in which suction source 78 is provided, is in a vicinity of the suction source), typically outside the body of the patient. In this latter configuration: (a) third pressure sensor 74 is integrated with suction source 78, or is positioned separately from suction source 78; and (b) third pressure sensor 74 is in fluid communication with a distal portion of lumen 20 distal to piston head 30, either via vent tube 38, or via a separate passageway in fluid communication with third pressure sensor 72 and the distal portion of lumen 20 (separate passageway not shown).

For some applications in which third pressure sensor 78 is in fluid communication with the distal portion of lumen 20 via vent tube 38, a source such as suction source 78 is adapted to periodically, such as once every 5 to 15 seconds, e.g., once every 10 seconds, generate a burst of fluid (i.e., liquid or gas) in vent tube 38, in order to clear from the tube any bodily material which may have entered the tube through opening 40. Similarly, for some applications in which third pressure sensor 78 is in fluid communication with the distal portion of lumen 20 via a separate passageway, an additional source of pressure coupled to a proximal end of the separate passageway periodically generates a burst of fluid in the separate passageway.

In some embodiments of the present invention, satisfactory performance of system 68 is attained by maintaining a pressure on the proximal side of piston head 30 at about 25 millibar gauge, a pressure on the distal side of piston head 30 at about 5 millibar gauge, and a pressure inside piston head 30 at about 20 millibar gauge. These values typically range, as appropriate, between about +10 and +50 millibar, −5 and +15 millibar, and +10 and +60 millibar, respectively.

For some applications, during distal advancement of system 68, the pressure inside piston head 30 is maintained within about 5 millibar of the pressure differential across either side of piston head 30. For example, using the exemplary numbers cited above, a pressured differential across the piston head is 25 millibar−5 millibar=20 millibar. By maintaining the pressure inside piston head 30 within 5 millibar of the pressure differential, the pressure inside piston head 30 would generally remain between 15 and 25 millibar. The pressure within piston head 30 is typically maintained near this differential pressure when piston head 30 comprises a flexible but substantially non-elastic material (e.g., a material such as a polyurethane that stretches less than 10% during inflation at less than 50 millibar). For embodiments in which piston head 30 comprises a flexible and elastic material (e.g., a material comprising silicone that stretches more than 10% during inflation at less than 50 millibar), the pressure within piston head 30 is typically greater than the differential pressure.

In an embodiment of the present invention, during distal advancement of system 68, the pressure inside piston head 30 is set to an initial value, such as between about 5 and 15 millibar, e.g., about 10 millibar. The pressure on the proximal side of piston head 30 is increased, typically gradually, and, simultaneously, the pressure inside piston head 30 is regulated to be the greater of (a) its initial value and (b) the pressure on the proximal side of piston head 30 plus a value such as a constant value. Typically, this constant value is between about 1 and about 5 millibar, e.g., between about 1.5 and about 2 millibar, such as about 2 millibar. Once system 68 begins advancing distally, the pressure on proximal head 30 generally declines or remains level, despite the continuous application of pressure by pressure source 16. A diameter of first passageway 14 is typically of a value sufficiently small to limit the increase over time of the pressure proximal to piston head 30 when system 68 is advancing distally. For example, the diameter of first passageway may be between about 3 and about 6 mm. In general, in this embodiment, substantially real-time control of the pressure in piston head 30 is exercised, while real-time control of the pressure in lumen 20 proximal to the piston head is not necessarily exercised.

Other combinations of the distal, proximal, and inside pressures for piston head 30 may be better suited for some applications, and the above numbers are not meant to limit the various operating pressures of embodiments of the current invention. Additionally, for some applications of the present invention, the various pressures acting on piston head 30 are regulated depending on where in the lumen the piston head is located.

Although FIG. 6 only shows a distal piston head, it is to be understood that the scope of the present invention includes a system comprising a proximal piston head, as shown in FIG. 1, comprising the various pressure control and measuring apparatus described hereinabove with regard to distal piston head 30 of FIG. 6.

Figure 7:
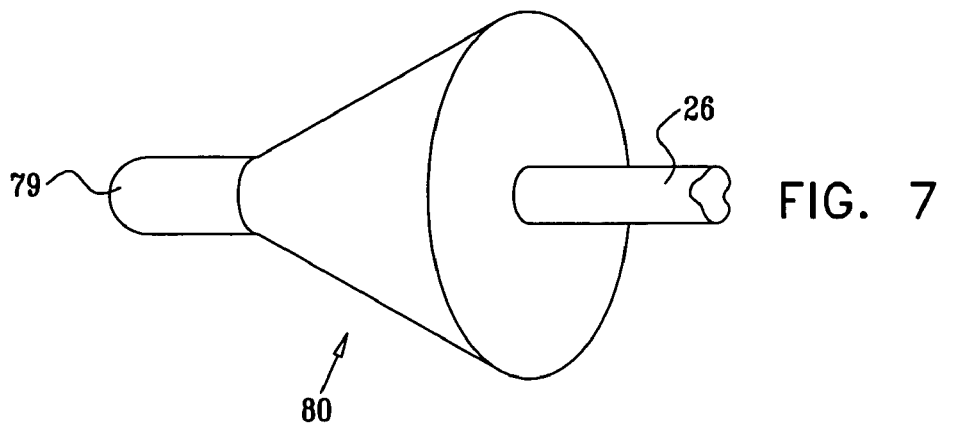
FIG. 7 is a pictorial illustration of an inflated conical balloon, which is adapted for use in accordance with an embodiment of the present invention.

Reference is now made to FIG. 7, which illustrates an inflatable piston head 80, constructed and operative in accordance with an embodiment of the present invention. Inflatable piston head 80 comprises an inflatable balloon that has the general form of a body of revolution about the axis formed by elongate carrier 26, wherein the distal end has a smaller diameter than the proximal end. Piston head 80 typically comprises a material that is flexible but substantially inelastic in the range of pressures typically encountered, such that the shape of the piston head is not substantially changed by elastic deformation when the piston head is inflated. Alternatively, piston head 80 comprises a flexible and elastic material. In some embodiments of the present invention, inflatable piston head 80 has the shape of a cone, as shown in FIG. 7. It is noted that whereas a cone is formed by rotating a straight line about an axis of revolution, other shapes for inflatable piston head 80 are formed by rotating curved lines about an axis of revolution. For example, a parabola or circular arc may be used to generate appropriate shapes. In the context of the present patent application and in the claims, all such shapes which become narrower towards their distal end are referred to as having a "distally-narrowing portion."

For some embodiments of the present invention, the base of inflatable piston head 80 is flat. In some other embodiments, the base of inflatable piston head 80 is curved, wherein the curvature may be either concave or convex.

Figure 8:
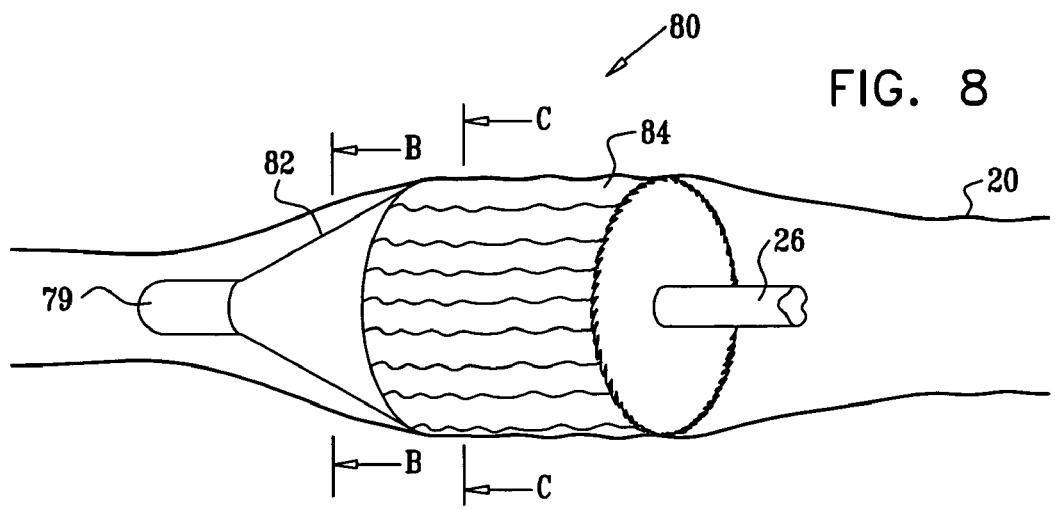
FIG. 8 is a pictorial illustration of a partially-inflated conical balloon in a body lumen, in accordance with an embodiment of the present invention.

FIG. 8 shows an application of inflatable piston head 80, in accordance with an embodiment of the present invention. Piston head 80 is typically inserted into lumen 20 in a deflated state and subsequently inflated until appropriate contact is made with the lumen. Due to the shape of inflatable piston head 80, most of a fully-inflated portion 82 of the piston head is not in substantial contact with lumen 20, while a partially-inflated portion 84 of the piston head is in contact with lumen 20, once the piston head is fully pressurized. A good seal between piston head 80 and lumen 20 is typically obtained where fully-inflated portion 82 meets partially-inflated portion 84.

Figures 9A, 9B:
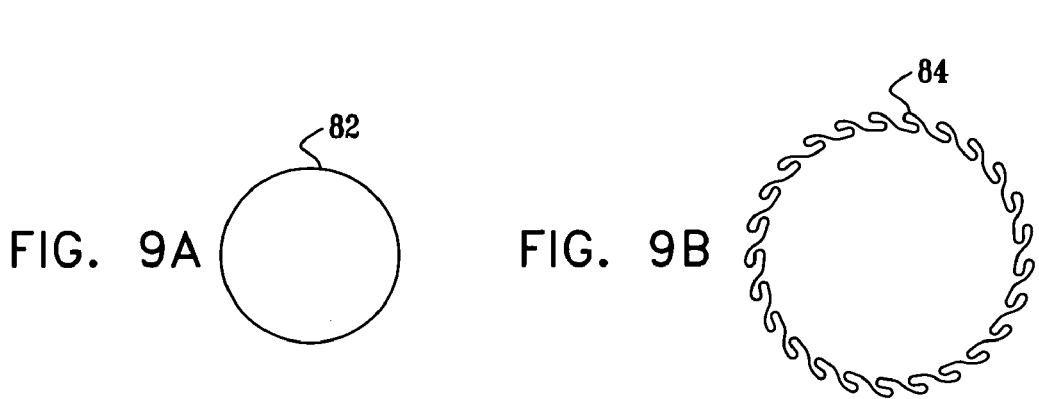
FIG. 9A is a pictorial illustration of the cross-section of a fully inflated portion of a conical balloon, in accordance with an embodiment of the present invention.
FIG. 9B is a pictorial illustration of the cross-section of a partially inflated portion of a conical balloon, in accordance with an embodiment of the present invention.

FIGS. 9A and 9B show cross-sections of the fully-inflated portion and the partially-inflated portion, respectively, in accordance with an embodiment of the present invention. Resistance of lumen 20 to radial expansion prevents the entire piston head from fully inflating (e.g., as shown in FIG. 7). Thus, partially-inflated portion 84 typically becomes somewhat wrinkled along the length of its contact with lumen 20.

Inflatable piston head 80 is regulated to respond to changes in the diameter of lumen 20 by inflating more as the lumen diameter increases, and by deflating as the lumen diameter decreases, all while maintaining satisfactory contact with the lumen. Since inflatable piston head 80 is typically made of a substantially inelastic material, a relatively modest pressure is needed to inflate the piston head. The inflation pressure is chosen to maintain an appropriate seal between the piston head and the lumen, without undue pressure on the lumen.

Figure 10A:
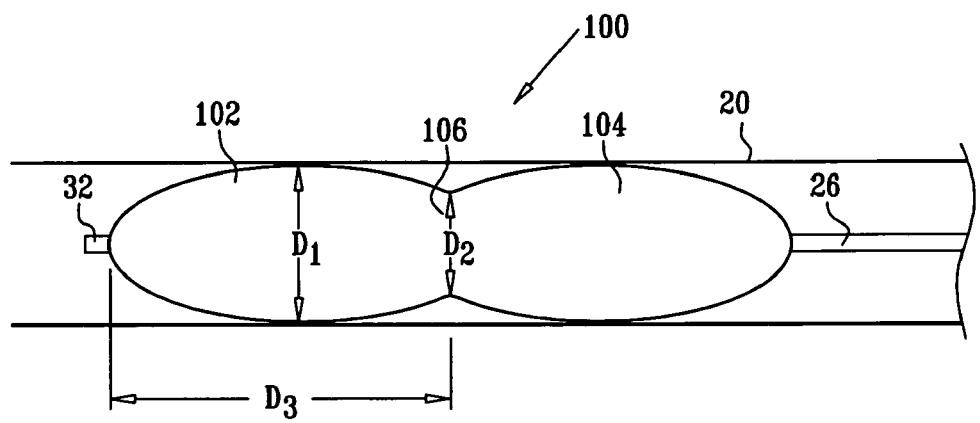
FIGS. 10A and 10B are pictorial illustrations of a system for use in a body lumen, constructed and operative in accordance with an embodiment of the present invention.
Figure 10B:
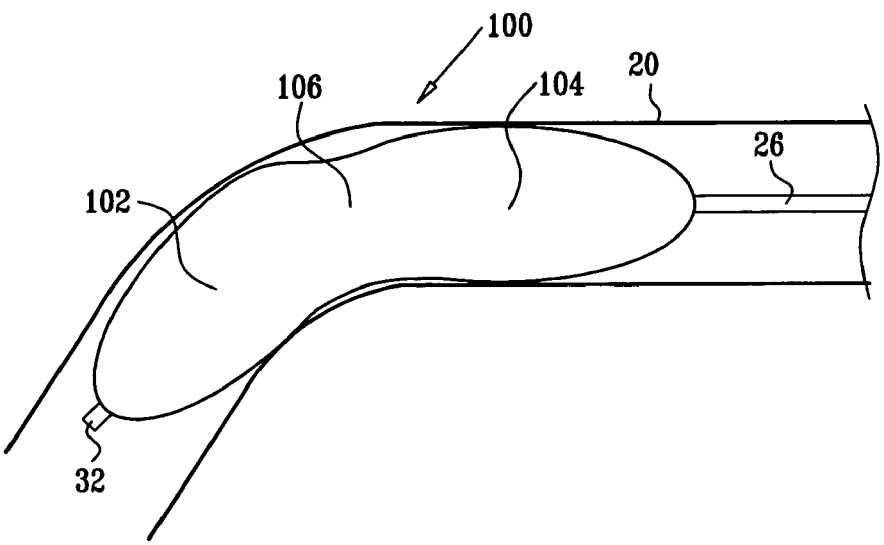

FIGS. 10A and 10B are pictorial illustrations of a multi-lobed piston head 100 for use in body lumen 20, constructed and operative in accordance with an embodiment of the present invention. Except for differences as noted, apparatus and techniques described hereinabove with respect to other piston heads are typically adapted for use with piston head 100.

Piston head 100 comprises a distal lobe 102 and a proximal lobe 104. Lobes 102 and 104 articulate at an intermediate portion 106. In an embodiment, dimensions of piston head 100 include: (a) a diameter D1 of distal lobe 102, which is substantially equal to the diameter of lumen 20, so as to make a satisfactory seal therewith, (b) a diameter D2 of intermediate portion 106, ranging from about 10% to 40% of D1, and (c) a length D3 of distal lobe 102, ranging from about 3 to 5 cm. It is noted that although multi-lobed piston head 100 only comprises two lobes, the scope of the present invention includes multi-lobed piston heads having more lobes (e.g., 3, 4, or 5 lobes).

Distal and proximal lobes 102 and 104 are in fluid communication with each other through intermediate portion 106. In steady state, as well as at the levels of movement typically encountered during advancement through the colon, the pressure within lobe 102 is substantially the same as the pressure within lobe 104. Thus, passageway 34 and fluid pressure source 36 (FIG. 2) regulate the pressure within both lobes substantially simultaneously. The diameters of the two lobes, however, typically vary independently, in response to changes in the shape of lumen 20 adjacent to each of the lobes.

Typically, as with all of the inflatable piston heads described herein, fluid is actively added to or removed from the piston head to maintain a generally constant pressure within the piston head.

In an embodiment of the present invention, piston head 30 and/or carrier 26 of system 10 and/or system 68 comprises a low friction coating, which acts to reduce the friction between piston head 30 and lumen 20, thereby easing the movement of piston head 30 and/or carrier 26 in lumen 20. For example, piston head 30 and/or carrier 26 may comprise a biocompatible low friction coating. Alternatively or additionally, piston head 30 and/or carrier 26 comprises a hydrophilic coating. Additionally or alternatively, the low friction coating comprises a suitable lubricant.

Figure 11A:
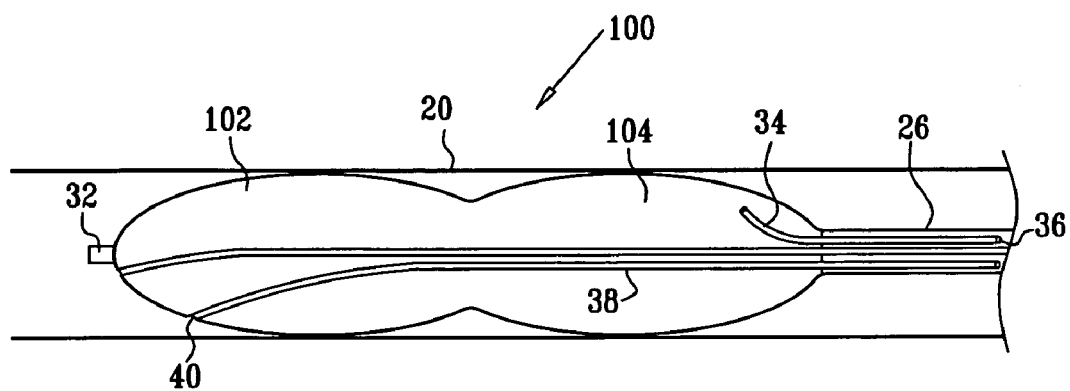
FIGS. 11A and 11B are pictorial illustrations of the multi-lobed piston head of FIGS. 10A and 10B, in accordance with an embodiment of the present invention.
Figure 11B:
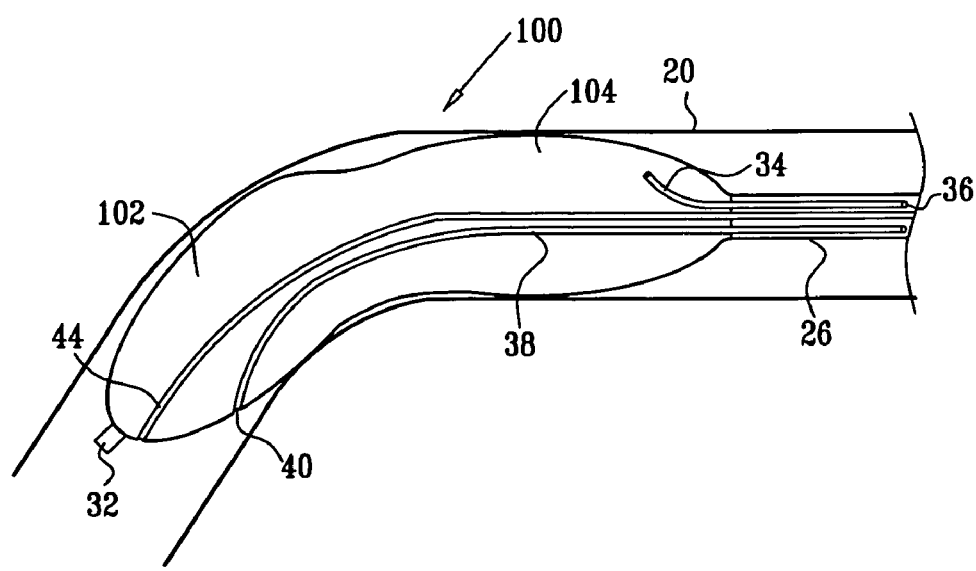

FIGS. 11A and 11B are pictorial illustrations of multi-lobed piston head 100, in accordance with an embodiment of the present invention. In FIGS. 11A and 11B, the following tubes described hereinabove are shown:

second passageway 34 in fluid communication with both lobes 102 and 104 of piston head 100, connected to source of fluid pressure 36;

vent tube 38, passing through lobes 102 and 104 of piston head 100, and having opening 40 distal to piston head 100 through which fluid is ventable to the outside;

fluid supply tube 44, passing through piston head 100, for cleaning the area near image-capturing device 32, or in combination with vent tube 38, for cleaning body lumen 20 itself.

Second passageway 34, vent tube 38, and fluid supply tube 44 are typically flexible, which allows for the bending of piston head 100, as shown in FIG. 11B.

FIG. 12 is a schematic cross-sectional illustration of an optical system 220, in accordance with an embodiment of the present invention. For some applications, image-capturing device 32 comprises optical system 220. Optical system 220 comprises an optical assembly 230 and an image sensor 232, such as a CCD or CMOS sensor.

Optical system 220 is typically configured to enable simultaneous forward and omnidirectional lateral viewing. Light arriving from the forward end of an optical member 234, and light arriving from the lateral surface of the optical member travel through substantially separate, non-overlapping optical paths. The forward light and the lateral light are typically (but not necessarily) processed to create two separate images, rather than a unified image. For some applications, the forward view is used primarily for navigation within a body region, while the omnidirectional lateral view is used primarily for inspection of the body region.

Optical assembly 230 comprises, at a distal end thereof, a convex mirror 240 having a rotational shape that has the same rotation axis as optical member 234. Optical member 234 is typically shaped so as to define a distal indentation 244 at the distal end of the optical member, i.e., through a central portion of mirror 240. Alternatively, optical member 234 is shaped without indentation 244, but instead mirror 240 includes a non-mirrored portion in the center thereof.

Typically, optical assembly 230 further comprises a distal lens 252 that has the same rotation axis as optical member 234. For some applications, optical assembly 230 further comprises one or more proximal lenses 258, e.g., two proximal lenses 258. Proximal lenses 258 are positioned between optical member 234 and image sensor 232, so as to focus light from the optical member onto the image sensor.

For some applications, optical system 220 is configured to enable omnidirectional lateral viewing, without enabling forward viewing.

For some applications, a hydrophobic coating is applied to one or more of the transparent surfaces of optical assembly 220 that are in contact with body lumen 20.

Techniques described herein may be performed in combination with techniques described in U.S. Provisional Patent Application 60/571,438, filed May 14, 2004, entitled, "Omnidirectional and forward-looking imaging device," which is assigned to the assignee of the present application and is incorporated herein by reference.

Reference is now made to FIGS. 13A and 13B, which are pictorial illustrations of a system 310 (not to scale), in accordance with an embodiment of the present invention. System 310 is generally similar to system 10 and/or system 68, except as described hereinbelow. Image-capturing device 32 of system 310 typically comprises optical system 220, described hereinabove with reference to FIG. 12, or another omnidirectional imaging device. System 310 is typically advanced distally into lumen 20 using techniques described hereinabove with reference to systems 10 and/or 68.

System 310 is withdrawn in a proximal direction by: (a) inflating lumen 20, using conventional inflation techniques for withdrawing endoscopes, and (b) pulling carrier 26 in a proximal direction. During withdrawal, the distal end of the system sometimes comes near or in contact with the wall of lumen 20, as shown in FIG. 13A. For example, lumen 20 may be inflated to a diameter D1 of between about 40 and about 70 mm, and system 310 may have an initial distal diameter D2 in a vicinity of image-capturing device 32 of between about 8 and about 15 mm. When system 310 is near the wall of lumen 20, the distance between the lateral portion of optical system 220 of image-capturing device 32 may be less than the minimum focal length necessary for clear omnidirectional lateral viewing.

System 310 comprises an inflation element 320, which is adapted to increase the distal diameter of system 310 from D2 (FIG. 13A) to D3 (FIG. 13B). D3 is typically between about 30 and about 45 mm. This increased distal diameter ensures that image-capturing device 32 is a distance from the wall of lumen 20 sufficient to enable focusing of the omnidirectional lateral image. For example, this increased distal diameter may ensure that a central axis of image-capturing device 32 is at least a distance D4 of 15 mm from the wall of lumen 20. For some applications, inflation element 320 comprises a sponge, which expands, for example, when exposed to liquid. Alternatively, inflation element 320 comprises a set of inflatable or expandable rings. Further alternatively, inflation element 320 comprises an inflatable balloon, which is typically contained within the body of system 310.

Figure 14:
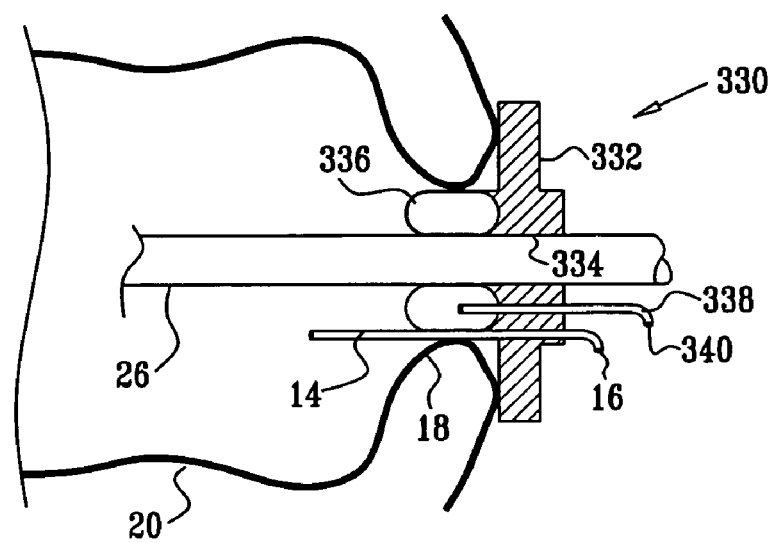
FIG. 14 is a schematic illustration of an inserter, in accordance with an embodiment of the present invention.

Reference is now made to FIG. 14, which is a schematic illustration of an inserter 330 for use with system 10 and/or system 68, in accordance with an embodiment of the present invention. Inserter 330 is adapted to be at least partially insertable into proximal opening 18 (e.g., the rectum) of body lumen 20 (e.g., the colon). Inserter 330 typically comprises an annular ring 332 for abutting against proximal opening 18, and an annular balloon 336 that is coupled to ring 332. Ring 332 and balloon 336 are shaped so as to define a bore 334 through which carrier 26 is arranged for sliding movement. Balloon 336 expands to form a seal between the balloon and the wall of lumen 20 in a vicinity of proximal opening 18, thereby helping maintain positive pressure created within body lumen 20.

Inserter 330 comprises first passageway 14 connected to fluid pressure source 16 (as described hereinabove with reference to FIGS. 1-3, for example), and a tube 338 for applying a positive pressure to inflate balloon 336. Tube 338 is connected to a fluid pressure source 340, which may comprise a powered fluid pressure source (such as is available in an operating room) or a manually-operated fluid pressure source (such as a syringe). When fluid pressure source 340 comprises a syringe, the syringe is typically removed after balloon 336 has been inflated, and tube 338 and/or balloon 336 is sealed to maintain the pressure, e.g., using a check valve (valve not shown). For some applications, pressure source 16 and pressure source 340 are derived from a common fluid pressure source.

Figure 15:
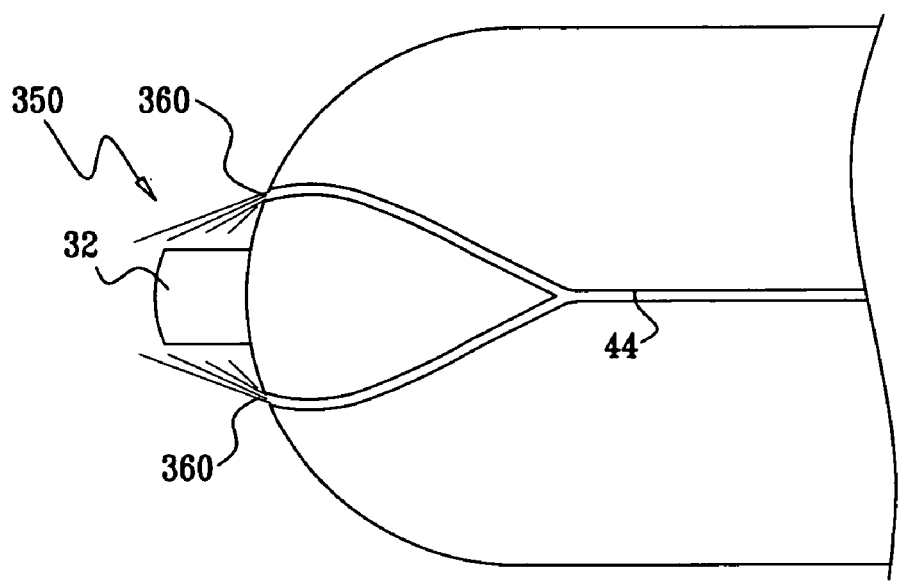
FIG. 15 is a schematic illustration of a cleaning system, in accordance with an embodiment of the present invention.

Reference is now made to FIG. 15, which is a schematic illustration of a cleaning system 350 for use with system 10 and/or system 68, in accordance with an embodiment of the present invention. Cleaning system 350 is shaped to define one or more openings 360 (e.g., between about 4 and about 10) coupled to fluid supply tube 44. Openings 360 are disposed circumferentially about the distal end of carrier 26, and oriented so that they spray at least a portion of image-capturing device 32. For applications in which image-capturing device 32 comprises optical system 220, as described hereinabove with reference to FIG. 12, openings 360 are typically oriented to spray at least a portion of the lateral omnidirectional portion of optical assembly 230, and, optionally, a portion of the distal forward portion of the assembly. For some applications, openings 360 are positioned at a circumferential angle, so as to create a vortex around image-capturing device 32.

Although the piston head has been described in embodiments of the present invention as being in direct contact with the wall of the GI tract, the scope of the invention includes establishing contact between the piston head and the wall of the GI tract through an intermediary, such as a sheath surrounding the piston head.

Techniques described herein may be performed in conjunction with techniques described in the following patent applications, which are assigned to the assignee of the present application and are incorporated herein by reference: (a) U.S. patent application Ser. No. 10/838,648 to Gross et al., entitled, "Pressure-propelled system for body lumen," filed May 3, 2004, and (b) a U.S. provisional patent application to Gross et al., entitled, "Pressure-propelled system for body lumen," filed on or about Jan. 9, 2004.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use in a body lumen having a proximal opening, the apparatus comprising:
    first and second fluid pressure sources;
    an elongate carrier, adapted to be inserted through the proximal opening of the body lumen;
    an inflatable piston head coupled to a distal portion of the carrier, and adapted to form a pressure seal with a wall of the lumen after the carrier has been inserted into the lumen;
    a first passageway in fluid communication with the first pressure source and a proximal portion of the lumen proximal to the piston head;
    a second passageway in fluid communication with the second pressure source and the piston head;
    first and second pressure sensors, adapted to measure a first measurable pressure in the proximal portion of the lumen, and a second measurable pressure in the piston head, respectively; and
    a control unit, adapted to cause the piston bead to be advanced distally in the lumen by:
        while the first pressure source applies a first applied pressure to the proximal portion of the lumen,
        regulating the second measurable pressure in the piston head to be equal to the first measurable pressure in the proximal portion of the lumen plus a positive value, by driving the second pressure source to apply a second applied pressure.

2. The apparatus according to claim 1, wherein the lumen includes a gastrointestinal (GI) tract, and wherein the carrier is adapted to be inserted through the proximal opening of the GI tract.

3. The apparatus according to claim 2, comprising a third passageway in fluid communication with a portion of the GI tract distal to the piston head and a site outside the GI tract.

4. The apparatus according to claim 2, wherein the first passageway has a diameter of between 3 and 6 mm.

5. The apparatus according to claim 2, wherein the positive value is between 1 and 5 millibar.

6. The apparatus according to claim 2, wherein the control unit is adapted to set the second measurable pressure in the piston head at an initial value prior to application of the first applied pressure, by driving the second pressure source to apply the second applied pressure.

7. The apparatus according to claim 6, wherein the initial value is between 5 and 15 millibar, and wherein the control unit is adapted to set the second measurable pressure at between 5 and 15 millibar.

8. The apparatus according to claim 6, wherein the control unit is adapted to regulate the second measurable pressure to be equal to the greater of: (a) the initial value, and (b) the first measurable pressure plus the positive value.

9. The apparatus according to claim 1, wherein the piston head has a wall thickness of 10-100 microns.

10. A method comprising:
    forming a pressure seal between an inflatable piston head and a wall of a body lumen;
    measuring a first measurable pressure in a proximal portion of the lumen proximal to the piston head, and a second measurable pressure in the piston head; and
    advancing the piston head distally through the lumen by:
        applying a first applied pressure to the proximal portion of the lumen, and
        regulating the second measurable pressure in the piston head to be equal to the first measurable pressure in the proximal portion of the lumen plus a positive value, by applying a second applied pressure to piston bead.

11. The method according to claim 10, wherein the lumen includes a gastrointestinal (GI) tract, and wherein forming the pressure seal comprises forming the pressure seal between the piston head and the wall of the GI tract.

12. The method according to claim 11, wherein the positive value is between 1 and 5 millibar.

13. The method according to claim 11, wherein regulating the second measurable pressure comprises setting the second measurable pressure in the piston head at an initial value prior to application of the first applied pressure.

14. The method according to claim 13, wherein the initial value is between 5 and 15 millibar, and wherein setting the second measurable pressure comprises setting the second measurable pressure at between 5 and 15 millibar.

15. The method according to claim 13, wherein regulating the second measurable pressure comprises regulating the second measurable pressure to be equal to the greater of: (a) the initial value, and (b) the first measurable pressure plus the positive value.

* * * * *